US 7,850,697 B2

(12) United States Patent
Ross et al.

(10) Patent No.: US 7,850,697 B2
(45) Date of Patent: Dec. 14, 2010

(54) METHOD AND APPARATUS FOR REPLACING A SPINAL DISC

(75) Inventors: Raymond S. Ross, Sale (GB); Isador H. Lieberman, Pepper Pike, OH (US); Edward C. Benzel, Gates Mills, OH (US); Lee Strnad, Broadview Heights, OH (US); Keith Duke, Cleveland, OH (US); James M. Kuras, Macedonia, OH (US); Kari Zimmers, Solon, OH (US); Charles F. Birchall, Jr., Mentor, OH (US)

(73) Assignee: Axiomed Spine Corporation, Beachwood, OH (US)

( * ) Notice: Subject to any disclaimer, the term of this patent is extended or adjusted under 35 U.S.C. 154(b) by 694 days.

(21) Appl. No.: 11/294,925

(22) Filed: Dec. 6, 2005

(65) Prior Publication Data

US 2006/0149273 A1    Jul. 6, 2006

Related U.S. Application Data

(60) Provisional application No. 60/633,620, filed on Dec. 6, 2004.

(51) Int. Cl.
*A61B 17/70* (2006.01)
*A61B 17/88* (2006.01)
*A61F 2/44* (2006.01)

(52) U.S. Cl. ............... 606/86 R; 606/246; 606/279; 623/17.11; 623/17.15; 623/17.16

(58) Field of Classification Search ............ 606/60, 606/61, 86, 86 A, 99, 246, 279, 914; 623/17.11–17.16
See application file for complete search history.

(56) References Cited

U.S. PATENT DOCUMENTS

| 5,776,199 | A | * | 7/1998 | Michelson | 623/17.16 |
| 5,893,889 | A | | 4/1999 | Harrington | |
| 6,258,125 | B1 | * | 7/2001 | Paul et al. | 623/17.11 |
| 6,607,558 | B2 | * | 8/2003 | Kuras | 623/17.16 |
| 7,060,097 | B2 | | 6/2006 | Fraser et al. | |
| 7,128,761 | B2 | * | 10/2006 | Kuras et al. | 623/17.15 |
| 2002/0099443 | A1 | * | 7/2002 | Messerli et al. | 623/17.11 |
| 2003/0187506 | A1 | | 10/2003 | Ross | |
| 2004/0073307 | A1 | * | 4/2004 | Keller | 623/17.11 |
| 2004/0093087 | A1 | * | 5/2004 | Ferree et al. | 623/17.13 |
| 2004/0143331 | A1 | | 7/2004 | Errico et al. | |

(Continued)

FOREIGN PATENT DOCUMENTS

CA    2519926    10/2004

(Continued)

*Primary Examiner*—Thomas C Barrett
*Assistant Examiner*—Sameh Boles
(74) *Attorney, Agent, or Firm*—Tarolli, Sundheim, Covell & Tummino LLP

(57) ABSTRACT

An apparatus for replacing a spinal disc which has a rail extending from the outer surface to connect the apparatus to the first vertebra. The rail extends a first distance from the outer surface adjacent a first end. The rail extends a second distance from the outer surface adjacent a second end. The second distance is greater than the first distance. In another aspect of the apparatus, the first rail extends generally transverse to the first and second ends. The second rail extends generally transverse to the first rail.

7 Claims, 22 Drawing Sheets

U.S. PATENT DOCUMENTS

| | | |
|---|---|---|
| 2004/0143332 A1 * | 7/2004 | Krueger et al. ............ 623/17.14 |
| 2004/0215198 A1 | 10/2004 | Marnay et al. |
| 2004/0220567 A1 * | 11/2004 | Eisermann et al. ............ 606/61 |
| 2004/0267364 A1 * | 12/2004 | Carli et al. ................ 623/17.14 |
| 2005/0027300 A1 * | 2/2005 | Hawkins et al. ................ 606/86 |
| 2005/0033435 A1 * | 2/2005 | Belliard et al. ............ 623/17.14 |
| 2005/0038511 A1 * | 2/2005 | Martz et al. ............... 623/17.11 |
| 2005/0131542 A1 | 6/2005 | Benzel et al. |
| 2005/0131543 A1 | 6/2005 | Benzel et al. |
| 2006/0259146 A1 * | 11/2006 | Navarro et al. ............ 623/17.14 |
| 2007/0255414 A1 * | 11/2007 | Melkent et al. ............ 623/17.16 |

FOREIGN PATENT DOCUMENTS

| | | |
|---|---|---|
| WO | 2004089240 | 10/2004 |
| WO | 2004089259 | 10/2004 |

* cited by examiner

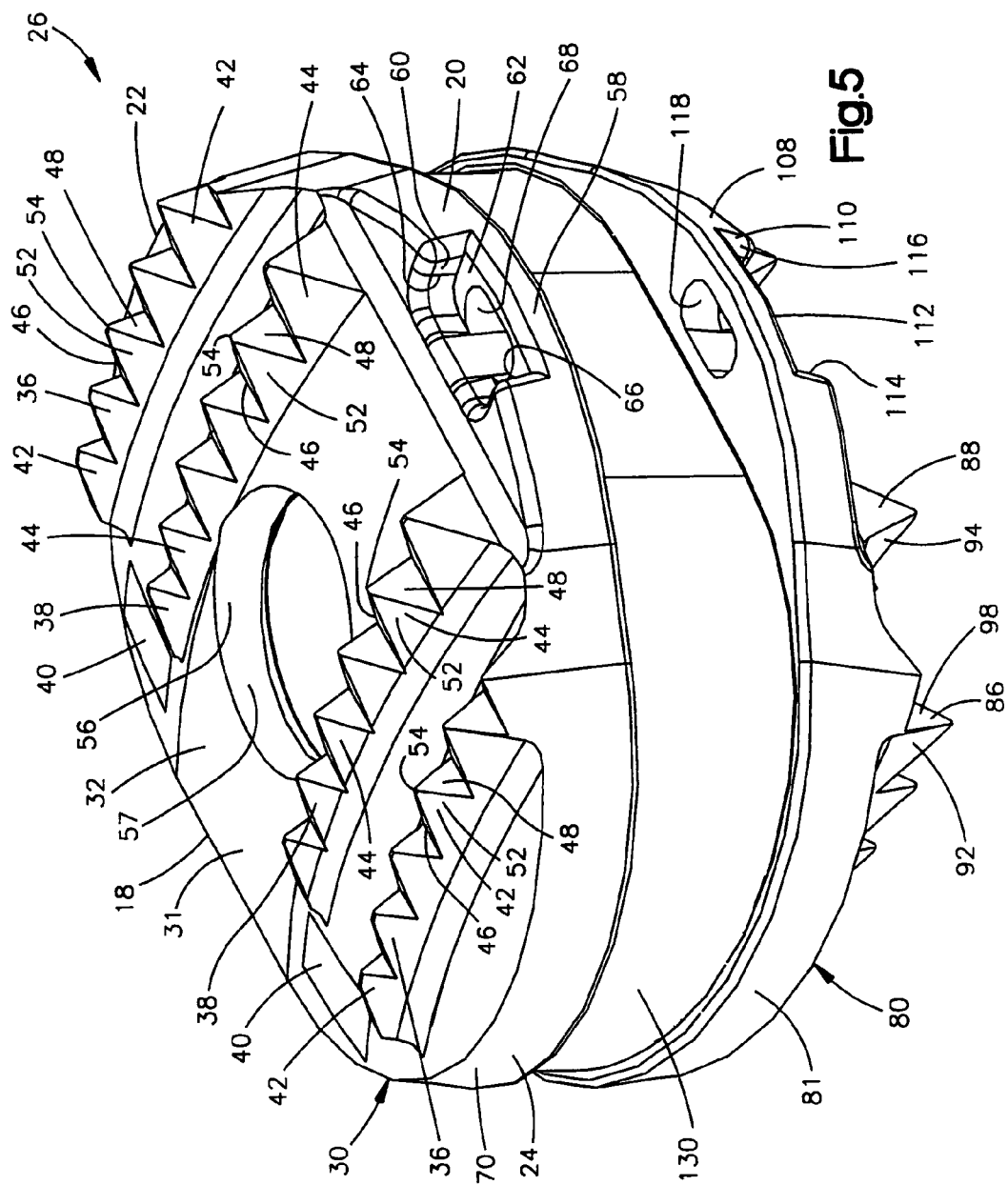

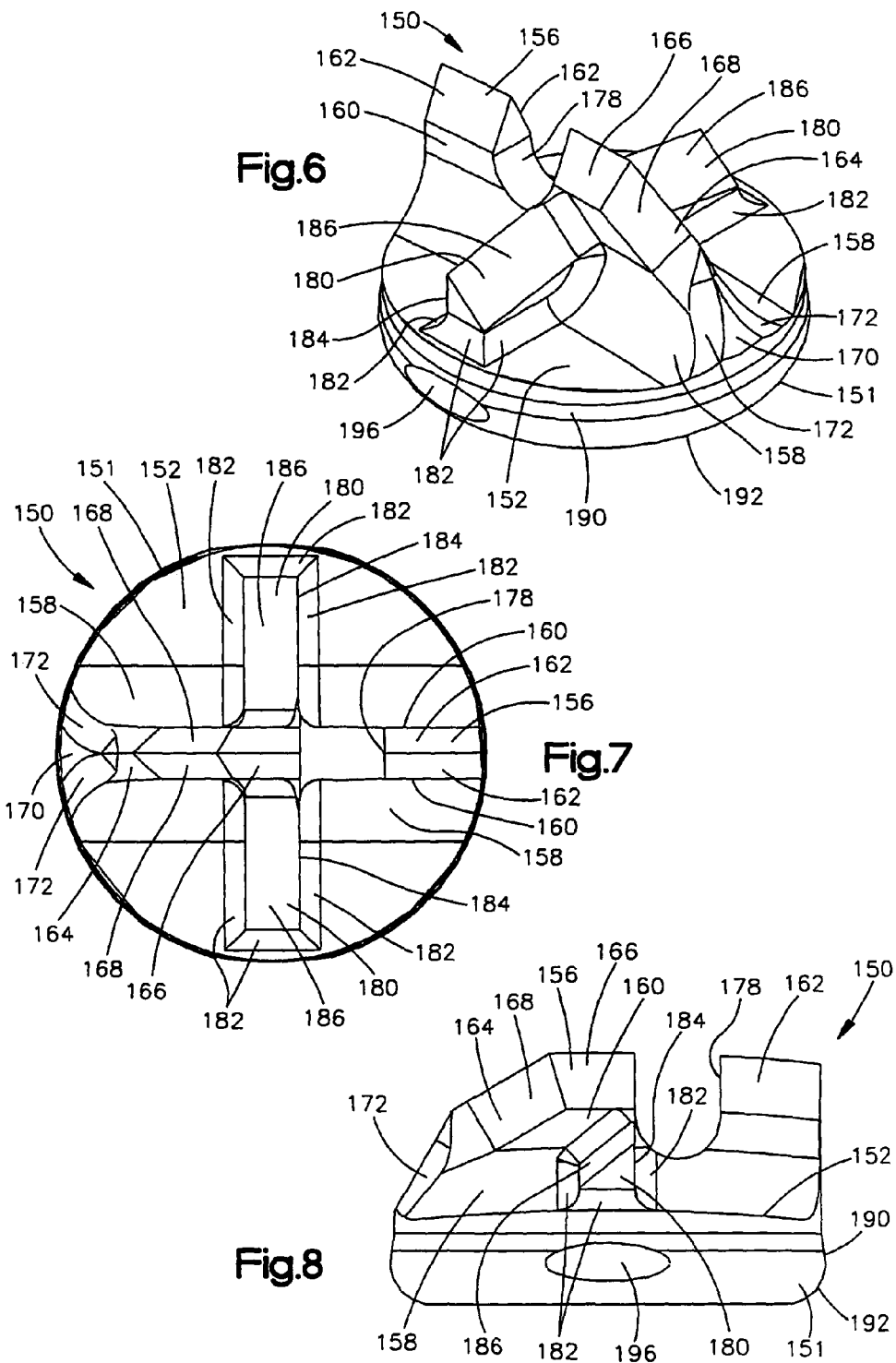

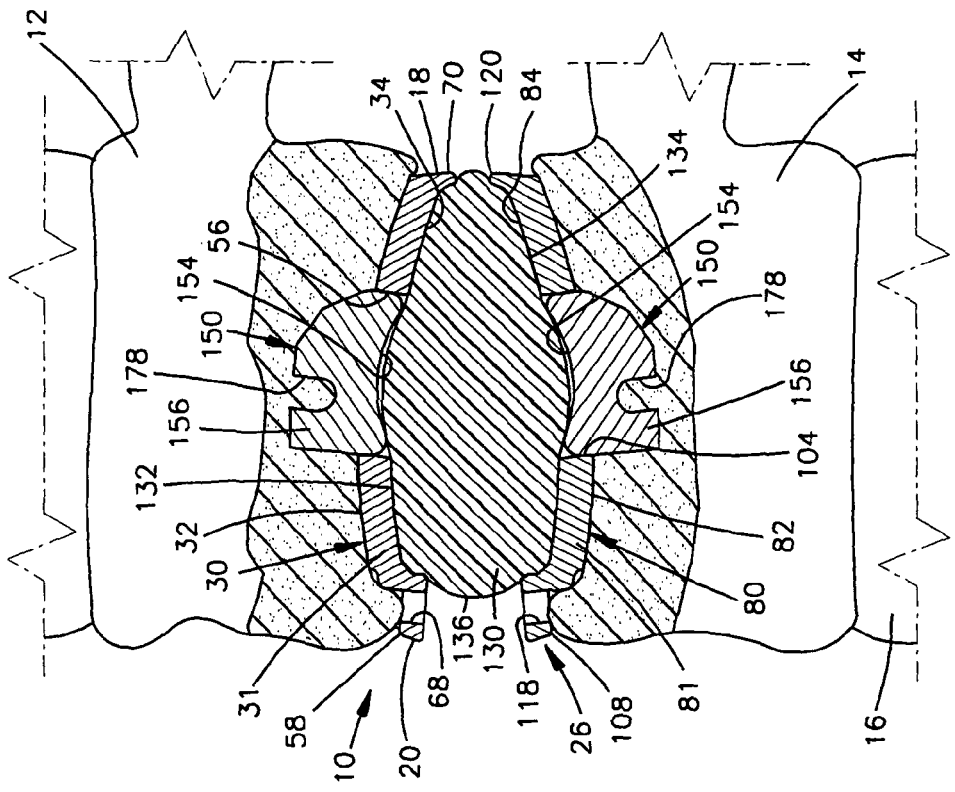
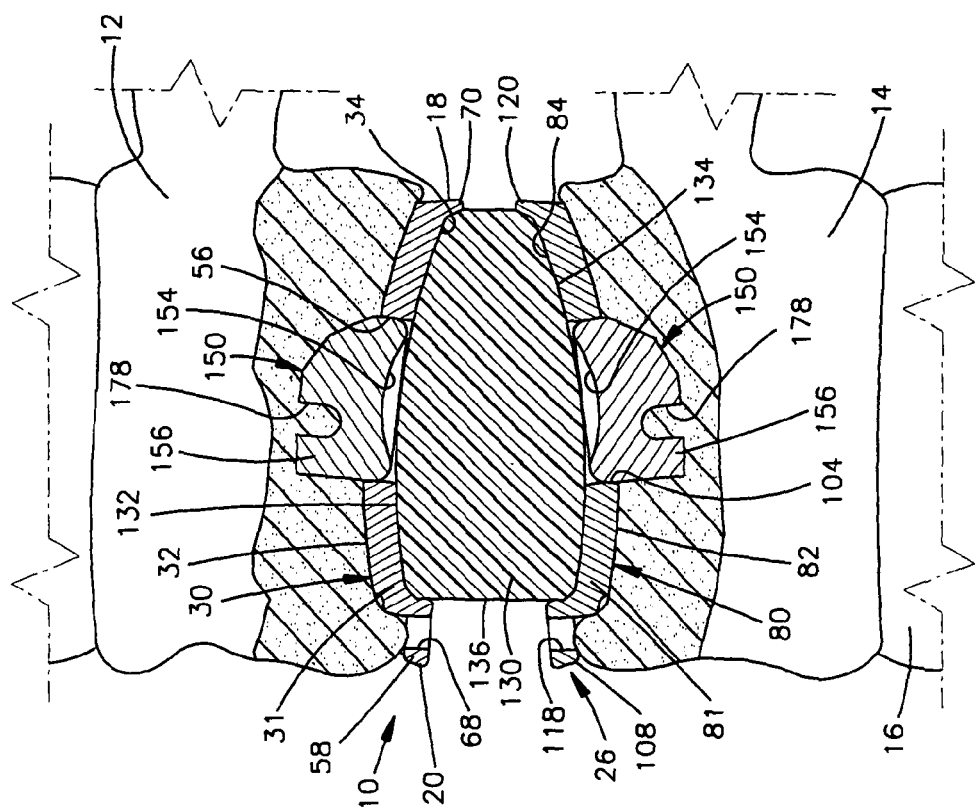

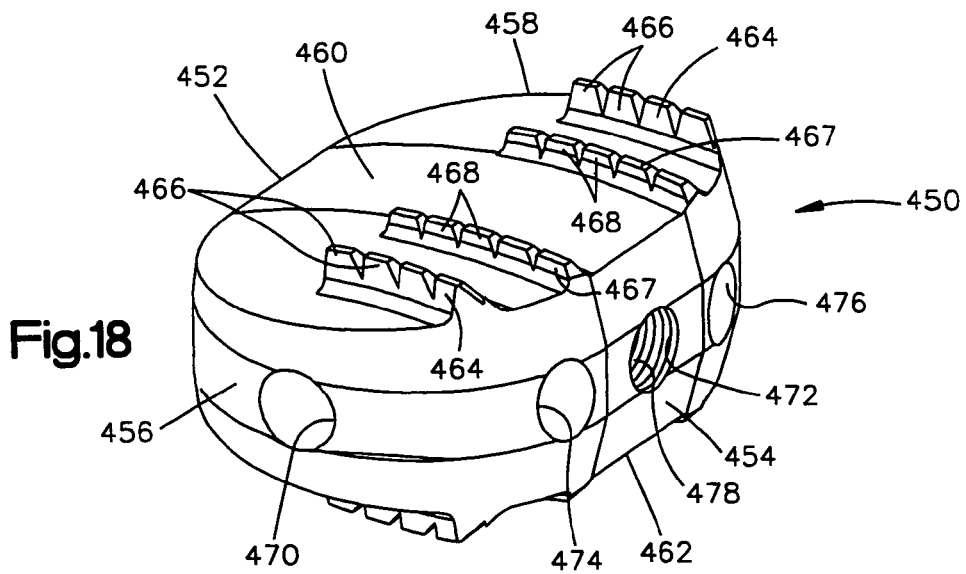
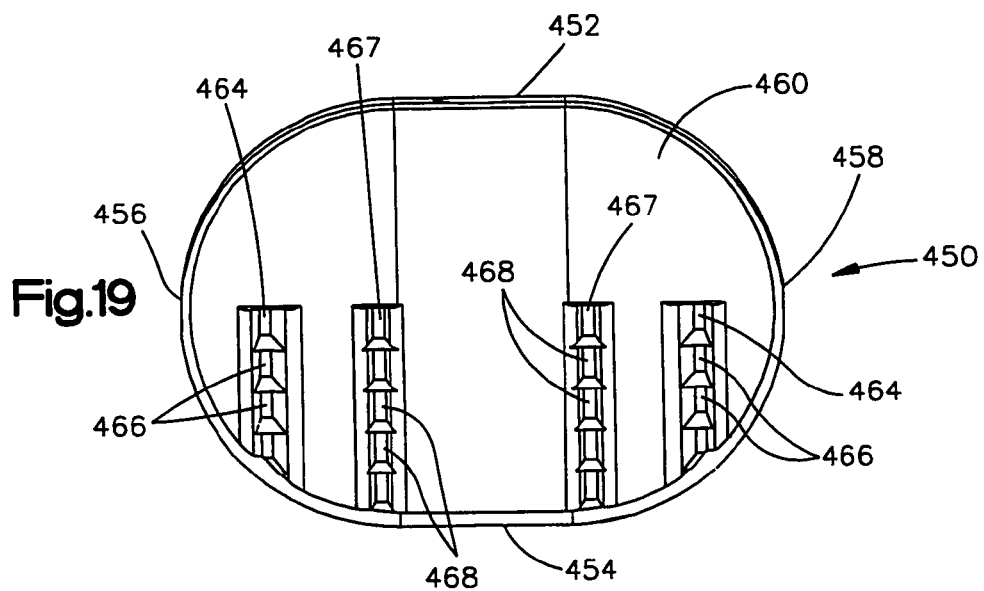
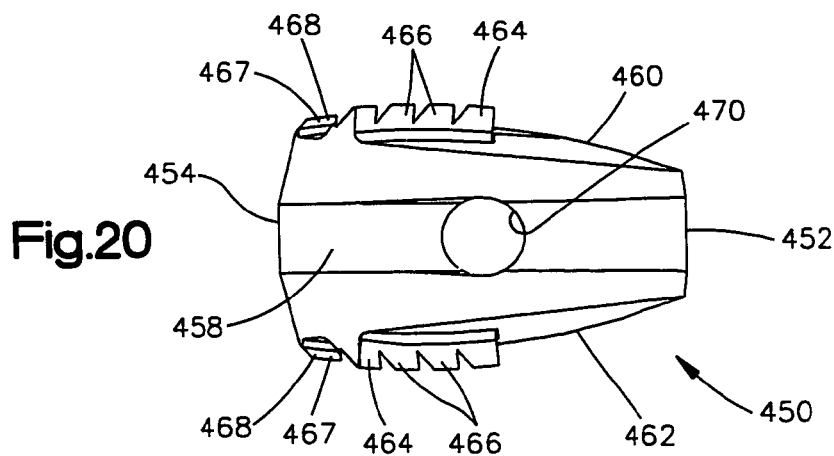

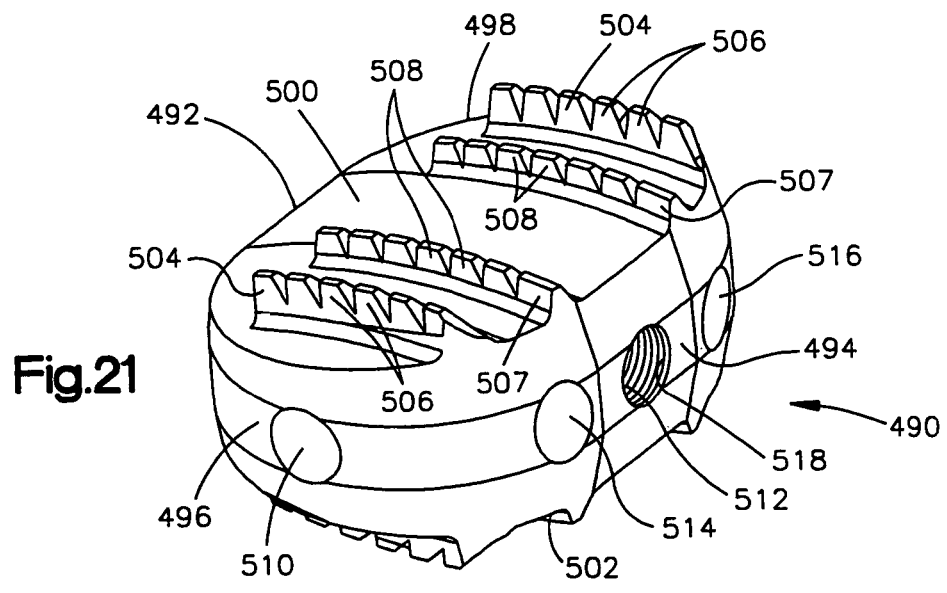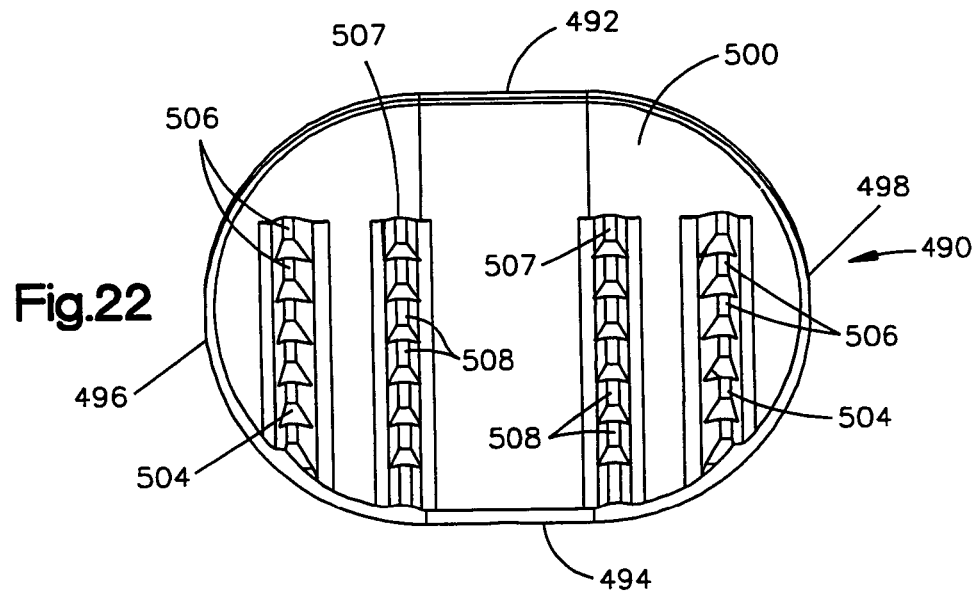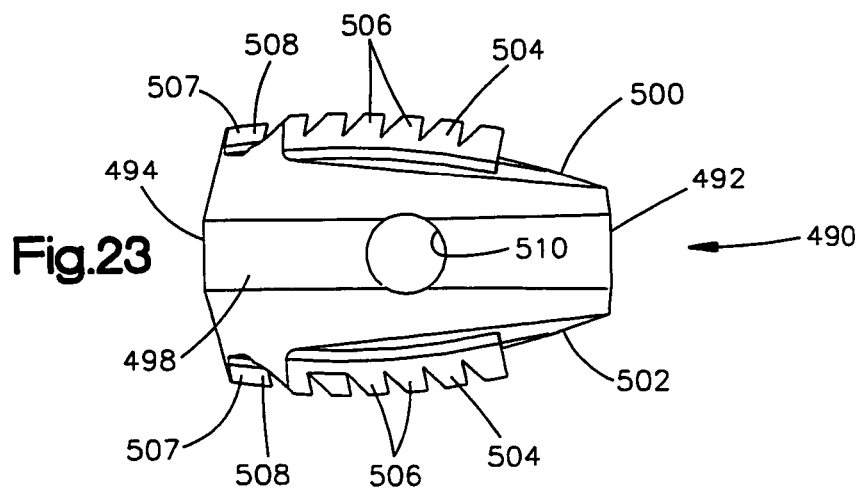

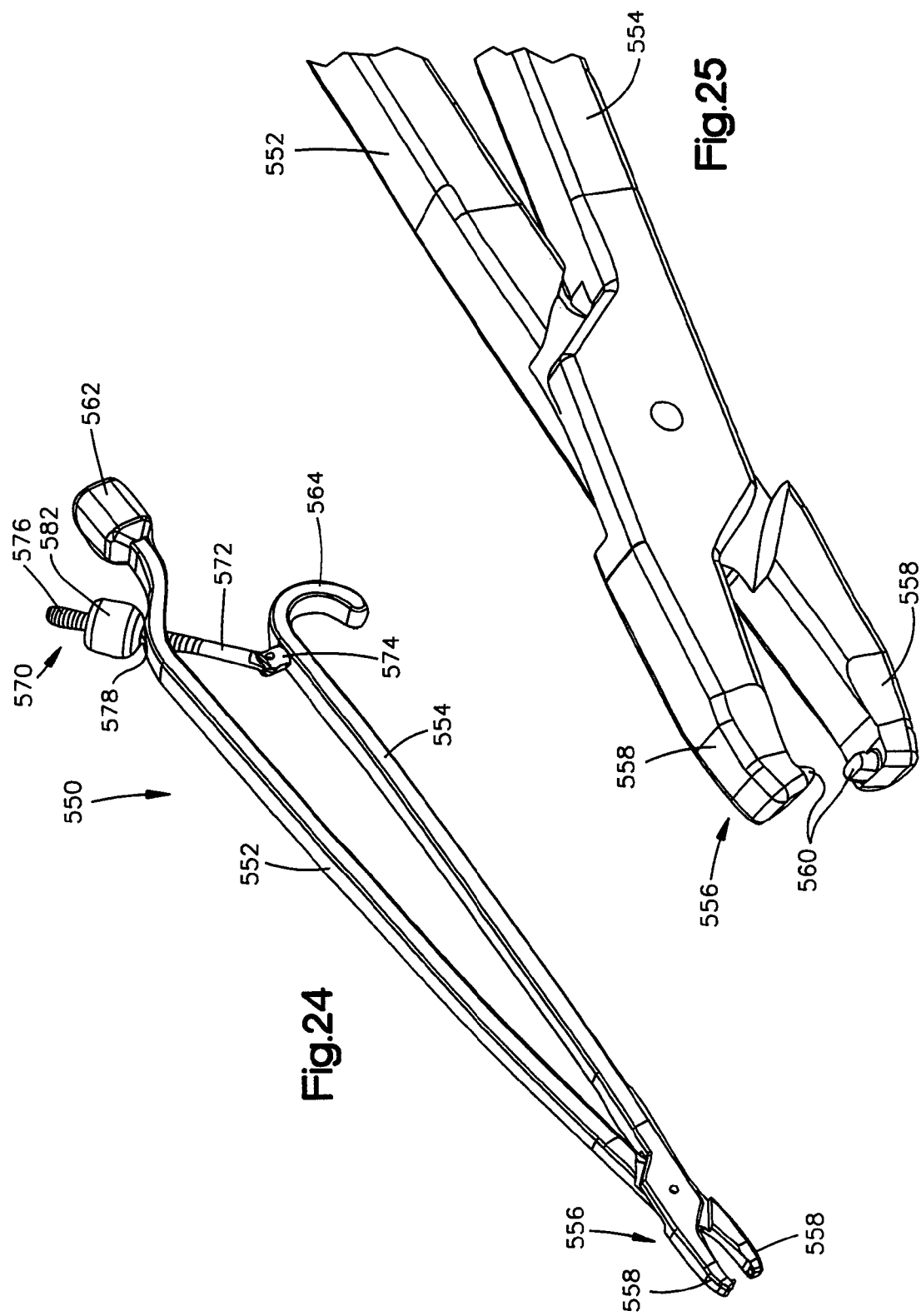

METHOD AND APPARATUS FOR REPLACING A SPINAL DISC

RELATED APPLICATION

This application is related to U.S. Provisional Patent Application Ser. No. 60/633,620, filed Dec. 6, 2004, the subject matter of which is incorporated herein by reference.

FIELD OF INVENTION

The present invention relates to a method and an apparatus for replacing a spinal disc in a spinal column, and more specifically, to a method for replacing a spinal disc in a spinal column using a guide assembly for guiding insertion of surgical instruments and an apparatus having projections extending from an outer surface for engaging vertebrae of the spinal column.

BACKGROUND OF THE INVENTION

It is known to replace a spinal disc with a prosthesis or artificial disc between first and second vertebrae of a spinal column. It is difficult to properly align surgical instruments for preparing the first and second vertebrae of the spinal column. The implant or artificial disc may include projections for engaging the first and second vertebrae.

SUMMARY OF THE INVENTION

A method for replacing a spinal disc between first and second vertebrae of a spinal column includes determining a reference point on the spinal column. A marker is connected to a vertebra of the spinal column at the reference point. The marker is engaged with a guide assembly for guiding insertion of a surgical instrument between the first and second vertebrae to prepare the space between the first and second vertebrae for receiving an apparatus between the first and second vertebrae. The apparatus is inserted between the first and second vertebrae.

The apparatus for replacing the spinal disc has a first end, a second opposite end, and first and second lateral sides extending between the first and second ends. An outer surface is engageable with the first vertebra of the spinal column. In accordance with one aspect of the apparatus, a rail extending from the outer surface is engageable with the first vertebra to connect the apparatus to the first vertebra. The rail extends a first distance from the outer surface adjacent the first end. The rail extends a second distance from the outer surface adjacent the second end. The second distance is greater than the first distance.

In accordance with another aspect of the apparatus, a first projection extending from the outer surface is engageable with the first vertebra to connect the apparatus to the first vertebra. The first projection extends from the outer surface a first distance. A second projection extending from the outer surface is engageable with the first vertebra to connect the apparatus to the first vertebra. The second projection is located closer to the second end than the first projection. The second projection extends from the outer surface a second distance greater than the first distance. In accordance with another aspect of the apparatus, first and second ribs extend from the outer surface. The first rib extends generally transverse to the first and second ends. The second rib extends generally transverse to the first rib.

BRIEF DESCRIPTION OF THE DRAWINGS

The foregoing and other features of the present invention will become apparent to one skilled in the art to which the present invention relates upon consideration of the following description of the invention with reference to the accompanying drawings, in which:

FIG. 5 is a pictorial view of an artificial disc of the apparatus of FIG. 1;

FIG. 6 is a pictorial view of a first embodiment of a mounting member of the apparatus of FIG. 1;

FIG. 7 is a schematic top view of the mounting member of FIG. 6;

FIG. 8 is a schematic side view of the mounting member of FIG. 6;

FIG. 9 is a schematic sectional view of the apparatus of FIG. 1 between adjacent vertebrae of a human spinal column;

FIG. 10 is a schematic sectional view of the apparatus of FIG. 1 between adjacent vertebrae of the spinal column showing the spinal column in compression;

FIG. 18 is pictorial view of a first cutter for use in preparing adjacent vertebrae for insertion of the apparatus of FIG. 1;

FIG. 19 is a schematic top view of the first cutter of FIG. 18;

FIG. 20 is a schematic side view of the first cutter of FIG. 18;

FIG. 21 is pictorial view of a second cutter for use in preparing adjacent vertebrae for insertion of the apparatus of FIG. 1;

FIG. 22 is a schematic top view of the second cutter of FIG. 21;

FIG. 23 is a schematic side view of the second cutter of FIG. 21;

FIG. 24 is a pictorial view of a surgical tool for use in inserting the apparatus of FIG. 1 between the adjacent vertebrae;

FIG. 25 is an enlarged view of a portion of the surgical tool of FIG. 24.

DESCRIPTION OF THE INVENTION

Figure 1:
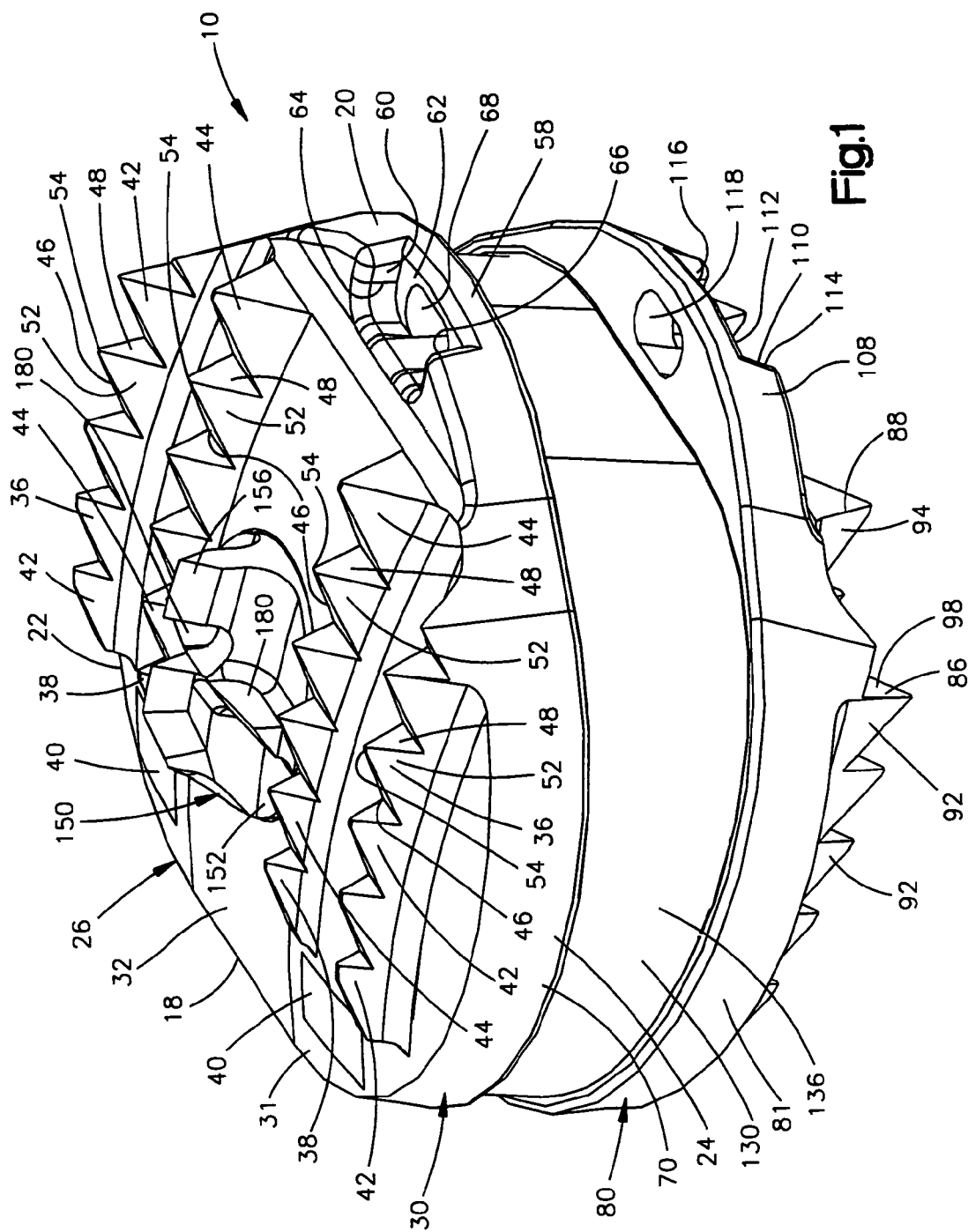
FIG. 1 is a pictorial view of an apparatus to replace a damaged spinal disc constructed in accordance with the present invention.
Figure 2:
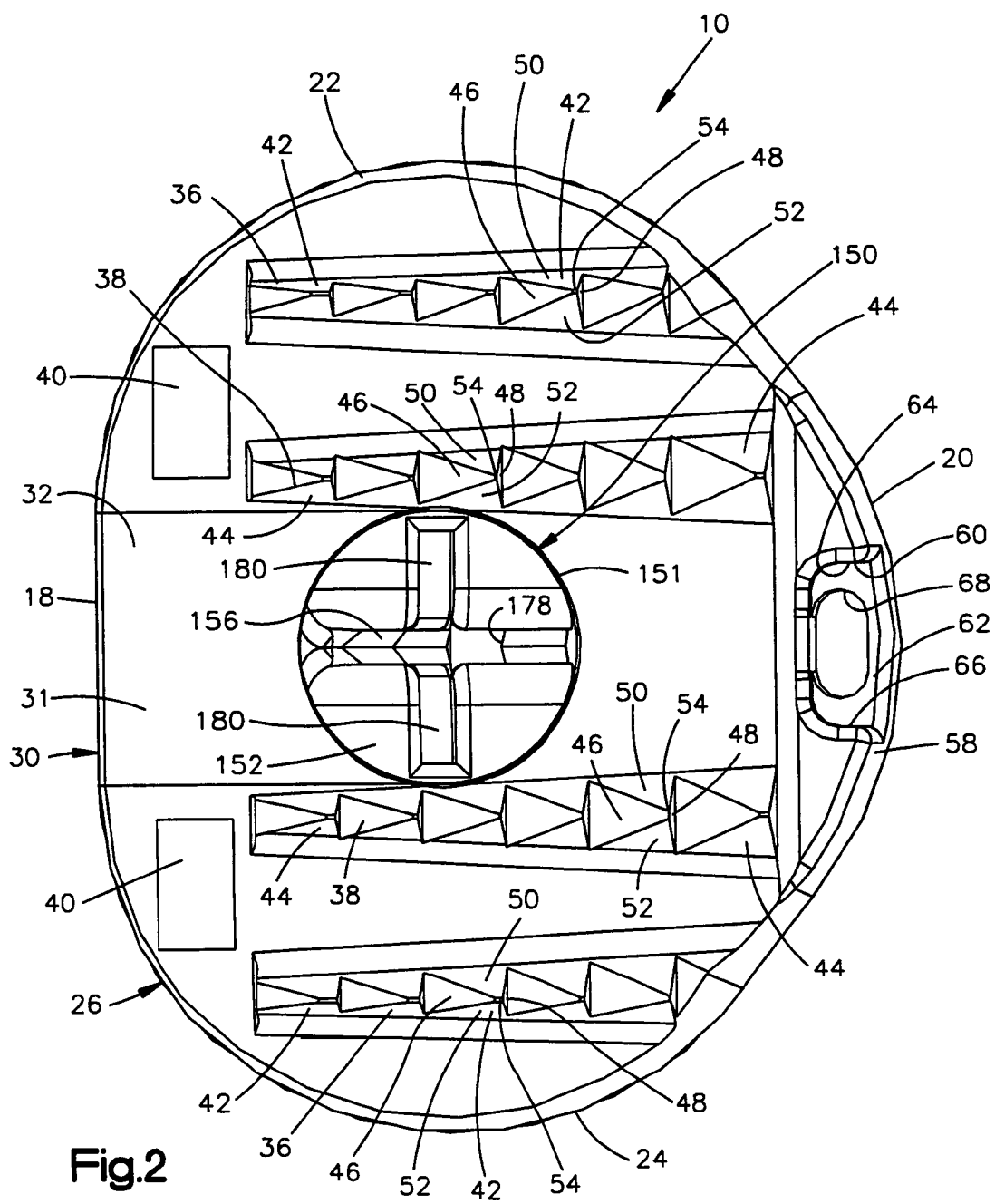
FIG. 2 is a schematic top view of the apparatus of FIG. 1.
Figure 3:
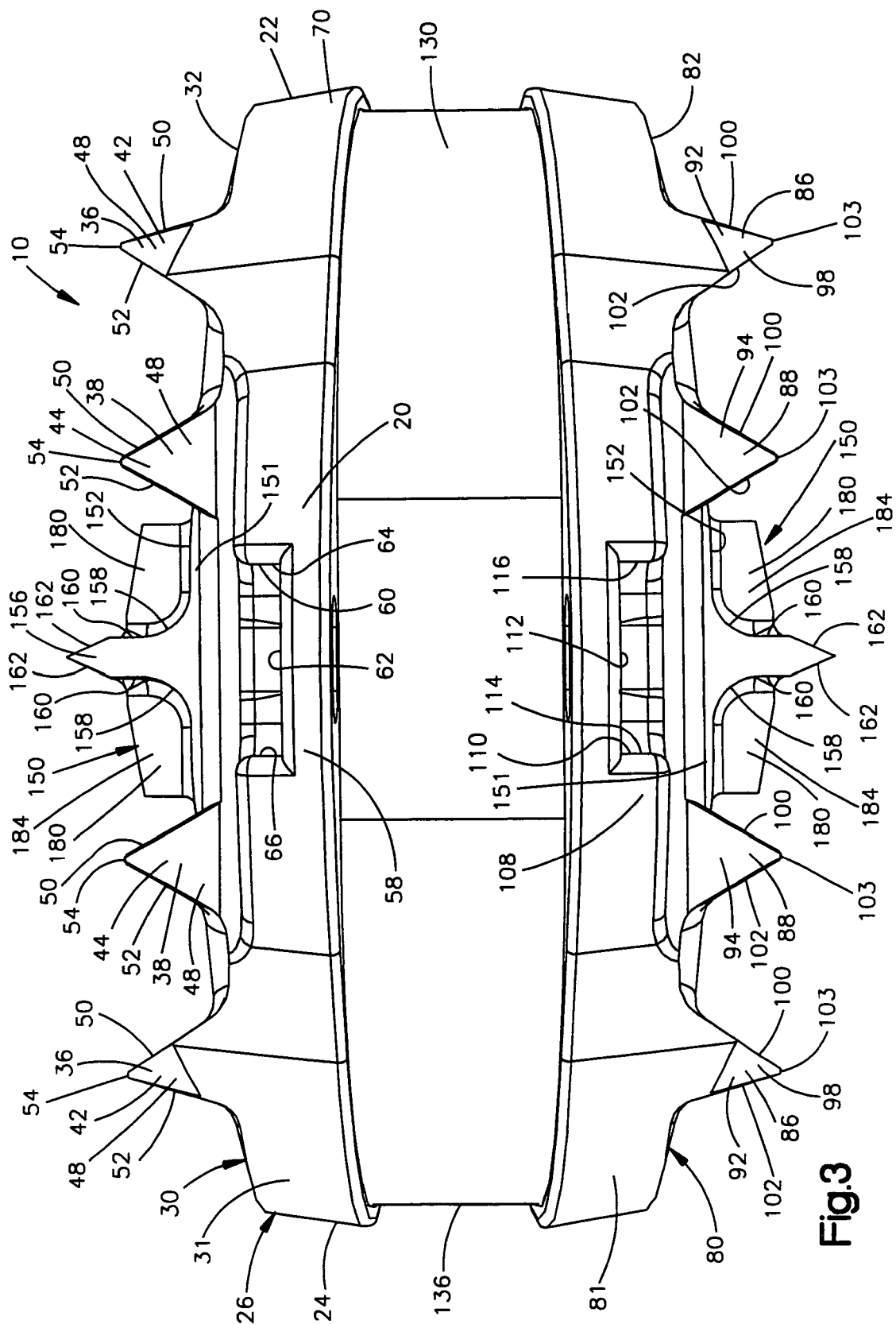
FIG. 3 is a schematic view showing an anterior end of the apparatus of FIG. 1.

The present invention relates to an apparatus, implant or prosthesis to replace a damaged or degenerated spinal disc in a spinal column of a human. FIGS. 1-4 illustrate an apparatus, implant or prosthesis 10 to replace a damaged or degenerated spinal disc in a spinal column. The apparatus 10 (FIG. 6) is used to replace a spinal disc between adjacent upper and lower vertebrae 12 and 14 of a human spinal column 16. The apparatus 10 (FIG. 2) has a first, distal or posterior end 18 and an opposite, second, proximal or anterior end 20. The apparatus 10 may be inserted between the vertebrae 12 and 14 with the first end 18 located adjacent a posterior side of the spine 16 and the second end 20 located adjacent an anterior side of the spine. The apparatus 10 includes first and second lateral sides 22 and 24 extending between the first and second ends 18 and 20.

The apparatus 10 (FIGS. 1-10) may include an artificial disc 26 and mounting members 150 that help connect the disc 26 to the adjacent vertebrae 12 and 14. The mounting members 150 may also help position the disc 26 relative to the vertebrae 12 and 14. The mounting members 150 may be connected to the disc 26 prior to inserting the apparatus 10 between the vertebrae 12 and 14. It is also contemplated that the mounting members 150 may be connected to the vertebrae 12 and 14 prior to inserting the disc 26 between the vertebrae.

Figure 4:
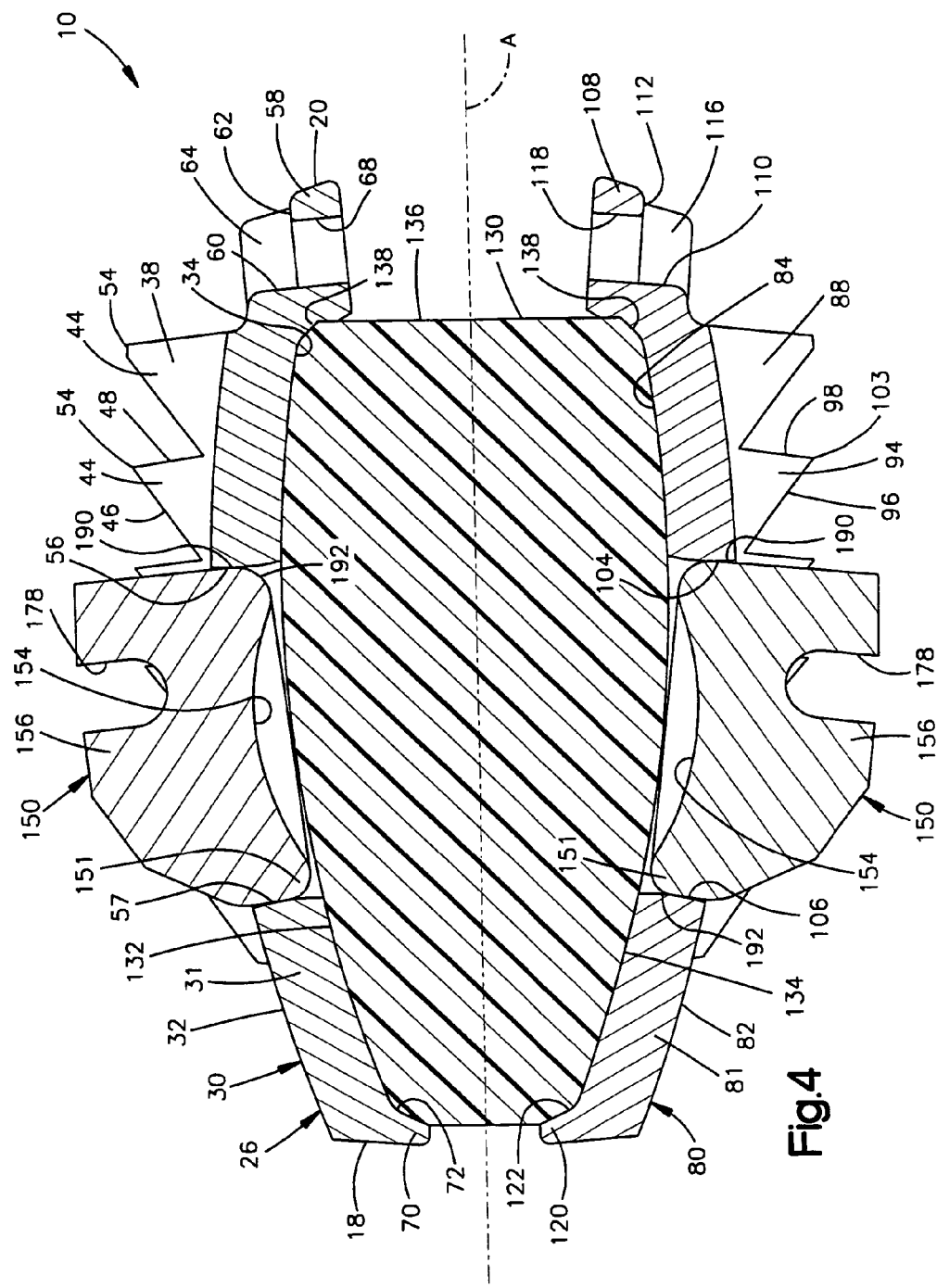
FIG. 4 is a sectional view of the apparatus of FIG. 1.

The apparatus 10 (FIG. 1) includes an upper or first retaining device 30, a lower or second retaining device 80 and a resilient core 130 interposed between and adhered to the retaining devices. The upper and lower retaining devices 30 and 80 are identical to each other and include mounting members 150. The apparatus 10 is symmetrical about a horizontally extending plane A (FIG. 4). The terms "upper" and "lower" are used herein with reference to the orientation of the apparatus 10 when in the human body, as illustrated in FIG. 9, to distinguish the two identical retaining devices for reference purposes.

The upper retaining device 30 (FIGS. 1-3) includes an upper or first retaining ring or member 31 and a mounting member 150. The artificial disc 26 includes the upper retaining member 31. The upper retaining member 31 is rigid and made of any desired biocompatible material such as a biocompatible metal or polymer. It is contemplated that the upper retaining member 31 may be made of a titanium alloy. It is also contemplated that the mounting member 150 may be formed as one-piece with the upper retaining member 31.

The upper retaining member 31 (FIG. 4) has an outer surface 32 engageable with the vertebra 12. An inner concave surface 34 of the upper retaining member 31 is affixed or bonded to the resilient core 130. The inner concave surface 34 may be fixedly connected to the core 130 in any desired manner. It is contemplated that the inner surface 34 may have beads (not shown) sintered on the inner surface or a texture (not shown) etched onto the inner surface to help connect the upper retaining member 31 to the core 130.

A plurality of rails or ribs 36 (FIGS. 1-3 and 5) extend from the outer surface 32 adjacent to the first and second lateral sides 22 and. A plurality of rails or ribs 38 extend from the outer surface 32 adjacent a central portion of the disc 26. Although the upper retaining member 31 is shown as having four rails 36 and 38, it is contemplated that the upper retaining member may have any number of rails 36 and 38. The rails 36 and 38 engage the vertebra 12 to help retain the apparatus 10 in position between the vertebrae 12 and 14. The outer surface 32 may have beads (not shown) sintered on the outer surface or a texture (not shown) etched onto the outer surface to further retain the apparatus 10 between the vertebrae 12 and 14. The rails 36 and 38 may not have beads or a texture to permit easy insertion of the apparatus 10 between the vertebrae 12 and 14. The outer surface 32 (FIG. 2) may include areas 40 adjacent the distal or posterior end 18 of the disc 26 that do not include beads or texture. The areas 40 may be located adjacent the distal or posterior ends of the rails or ribs 36 and 38. The areas 40 may permit easy insertion of the apparatus 10 between the vertebrae 12 and 14. It is contemplated that the areas 40 may have any desired shape, such as rectangular.

The rails 36 and 38 (FIGS. 1-4) extend generally parallel to each other from the second end 20 of the disc 26 toward the first end. It is contemplated that the rails 36 and 38 may extend in any desired direction. The direction in which the rails 36 and 38 extend is determined by the direction of insertion of the disc 26.

Each of the rails 36 includes a plurality of projections 42 extending from the outer surface 32. Although the rails 36 are shown with five projections 42, it is contemplated that the rails 36 may have any desired number of projections. The rails 36 taper from the posterior end 18 of the disc 26 to the anterior end 20. Accordingly, the projections 42 located closer to the posterior end 18 extend from the outer surface 32 a first distance and each adjacent projection 42 located closer to the anterior end 20 extends from the outer surface a second distance greater than the first distance.

Each of the rails 38 includes a plurality of projections 44 extending from the outer surface 32. Although the rails 38 are shown with six projections 44, it is contemplated that the rails 38 may have any desired number of projections. The rails 38 taper from the posterior end 18 of the disc 26 to the anterior end 20. Accordingly, the projections 44 located closer to the posterior end 18 extend from the outer surface 32 a first distance and each adjacent projection 44 located closer to the anterior end 20 extends from the outer surface a second distance greater than the first distance.

The projections 42 (FIG. 3) of the rails 36 adjacent the lateral sides 22 and 24 of the disc 26 extend from the outer surface 32 a distance that is greater than the distance that the projections 44 of the rails 38 extend from the surface. Accordingly, the projections 42 of the ribs 38 adjacent the lateral sides 22 and 24 of the disc 26 may extend into the vertebra 12 a greater distance than each adjacent projection 44 of the ribs 38. It is contemplated that the projections 42 and 44 may extend from the outer surface 32 any desired distances.

The projections 42 and 44 are substantially similar. Accordingly, only one projection 42 will be described in detail. The projection 42 (FIGS. 1 and 2) has a first or posterior surface 46 facing upward or outwardly and toward the first end 18 of the apparatus 10. The first surface 46 extends from the surface 32 at a first angle. A second or anterior surface 48 of the projection 42 faces upward or outwardly and toward the second end 20 of the apparatus 10. The second surface 48 extends from the surface 32 at a second angle. The second angle that the second surface 48 extends from the surface 32 is closer to perpendicular than the first angle that the first surface 46 extends from the surface 32. The projection 42 has a first lateral surface 50 facing upward or outwardly and toward the later side 22. The first lateral surface extends from the surface 32 at a third angle. A second lateral surface 52 faces upward or outwardly and toward the lateral side 24. The lateral surface 52 extends from the surface 32 at a fourth angle which is the same as the third angle. It is contemplated that the surfaces 46, 48, 50, and 52 may extend from the surface 32 at any desired angle. The projection 42 also includes an upper surface 54 that extends generally parallel to the surface 32. Each of the surfaces 46, 48, 50, and 52 has a trapezoidal shape. The first and second lateral surfaces 50 and 52 intersect the first surface 46 and the second surface 48. It is contemplated that the projections 42 and 44 may have any desired configuration.

An axially extending opening 56 (FIGS. 4-5) extends through the outer surface 32 and the inner surface 34 of the upper retaining member 31. The mounting member 150 extends into the opening 56 to connect the mounting member to the upper retaining member 31. The upper retaining member 31 has a frustoconical surface 57 at least partially defining the opening 56. An upper portion of the opening 56 has a first diameter and a lower portion of the opening has a second diameter smaller than the first diameter. The opening 56 is centrally located between the rails 38. Although the opening 56 is shown as being circular, it is contemplated that the opening may have any desired shape.

A flange portion 58 (FIGS. 1-5) extends from the upper retaining member 31 on the anterior end 20 of the disc 26. The flange portion 58 has a recess 60. The recess 60 is defined by a bottom surface 62 and side surfaces 64 and 66 extending upwardly from the bottom surface 62. An oval shaped slot 68 extends through the bottom surface 62 of the flange portion 58. The slot 68 extends in a direction transverse to the direction in which the rails 38 extend.

The inner concave surface 34 (FIG. 4) of the upper retaining member 31 is affixed or bonded to the resilient core 130. The upper retaining member 31 includes a peripheral flange portion 70 extending toward the lower retaining device 80. The flange 70 encircles the core 130. The flange 70 has a radially inner surface 72 facing the core 130. The surface 72 extends radially outwardly from the concave surface 34 and toward the lower retaining device 80. The surface 72 on the flange 70 is not connected to the core 130. Accordingly, the flange 70 may move relative to the core 130.

It is contemplated that the surface 72 may be spaced from the core 130 until a predetermined load is applied to the apparatus 10. The core 130 may deflect toward the surface 72 on the flange 70 when a load is applied to the apparatus 10 that moves the upper and lower retaining devices 30 and 80 relative to each other. When the predetermined load is applied to the apparatus 10 the core 130 may deflect into engagement with the surface 72 on the flange 70. When the core 130 engages the flange 70, the core stiffens since further deflection of the core is restricted by the flange.

The surface 72 of the flange 70 may have any desired configuration. The surface 72 may have a first portion that extends closer to the core 130 than a second portion so that the core engages the first portion of the surface 72 prior to engaging the second portion of the surface 72. Accordingly, the core 130 may engage different portions of the surface 72 as different loads are applied to the apparatus 10 to vary the stiffness of the core at the different loads.

It is contemplated that the retaining member 31 may have an inner surface (not shown) extending from the concave inner surface 34 to the opening 56 and spaced from the core 130 until a predetermined load is applied to the apparatus 10. When the predetermined load is applied to the apparatus 10, the core 130 deflects into engagement with the inner surface (not shown) extending from the concave surface 34 to the opening 56. When the core 130 engages the inner surface extending from the concave surface 34 to the opening 56, the core stiffens since further deflection of the core is restricted by the retaining member 31.

The lower retaining device 80 (FIGS. 1 and 2-5) is identical in configuration to the upper retaining device 30. The lower retaining device 80 includes a lower or second retaining member or ring 81 and a mounting member 150. The disc 26 includes the lower retaining member 81. It is contemplated that the mounting member 150 may be formed as one piece with the lower retaining member 81. The lower retaining member 81 is identical to the upper retaining member 31. Accordingly, the lower retaining member 81 will not be described in detail. The lower retaining member 81 is rigid and made from the same material as the upper retaining member 31, such as a titanium alloy.

The lower retaining member 81 (FIG. 4) has an outer surface 82 engageable with the vertebra 14. An inner concave surface 84 of the lower retaining member 81 is affixed or bonded to the resilient core 130. It is contemplated that the inner surface 84 may have beads (not shown) sintered on the inner surface or a texture (not shown) etched onto the inner surface to help connect the lower retaining member 81 to the core 130.

A plurality of rails or ribs 86 (FIGS. 1 and 3) extend from the outer surface 82 adjacent to the first and second lateral sides 22 and 24. A plurality of rails or ribs 88 extend from the outer surface 82 adjacent a central portion of the disc 26. The lower retaining member 81 may have any desired number of ribs 86 and 88. The rails 86 and 88 engage the vertebra 14 to help retain the apparatus 10 in position between the vertebrae 12 and 14. The outer surface 82 may have beads (not shown) sintered on the outer surface or a texture (not shown) etched onto the outer surface to further retain the apparatus 10 between the vertebrae 12 and 14. The rails 86 and 88 may not have beads or a texture to permit easy insertion of the apparatus 10 between the vertebrae 12 and 14. The outer surface 82 may include areas (not shown), similar to the areas 40 on the upper retaining member 31, adjacent the first end 18 of the disc 26 that do not include beads or texture. The areas may be located adjacent the distal or posterior ends of the rails or ribs 86 and 88. It is contemplated that the areas may have any desired shape, such as rectangular.

The rails 86 and 88 extend generally parallel to each other from the second end 20 of the disc 26 toward the first end 18. It is contemplated that the rails 86 and 88 may extend in any desired direction. The direction in which the rails 86 and 88 extend is determined by the direction of insertion of the disc 26.

Each of the rails 86 includes a plurality of projections 92 extending from the outer surface 82. The rails 86 may have any desired number of projections 92. The rails 86 taper from the first end 18 of the disc 26 to the second end 20. Accordingly, the projections 92 located closer to the posterior end 18 extend from the outer surface 82 a first distance and each adjacent projection 92 located closer to the anterior end 20 extends from the outer surface a second distance greater than the first distance.

Each of the rails 88 includes a plurality of projections 94 extending from the outer surface 82. The rails 88 may have any desired number of projections 94. The rails 88 taper from the posterior end 18 of the disc 26 to the anterior end 20. Accordingly, the projections 94 located closer to the posterior end 18 extend from the outer surface 82 a first distance and each adjacent projection 94 located closer to the anterior end 20 extends from the outer surface a second distance greater than the first distance.

The projections 92 (FIG. 3) of the rails 86 adjacent the lateral sides 22 and 24 of the disc 26 extend from the outer surface 82 a distance that is greater than the distance that the projections 94 of the rails 88 adjacent to the projections 92 of the rails 86 extend from the surface 82. Accordingly, the projections 92 of the rails 86 adjacent the lateral sides 22 and 24 of the disc 26 may extend into the vertebra 14 a greater distance than the projections 94 of the rails 88. The projections 92 and 94 may extend from the outer surface 82 any desired distance.

The projections 92 and 94 of the rails 86 and 88 are substantially similar to the projections 42 and 44 of the ribs 36 and 38. Accordingly, the projections 92 and 94 will not be described in detail. Each of the projections 92 and 94 (FIG. 4) has a first or posterior surface 96 facing downward or outwardly and toward the first end 18 of the apparatus. The first surface 96 extends from the surface 82 at a first angle. A second or anterior surface 98 faces downward or outwardly and toward the second end 20 of the apparatus 10. The second surface 98 extends from the surface 82 at a second angle. The second angle that the second surface 98 extends from the surface 82 is closer to perpendicular than the first angle that the first surface 96 extends from the surface 82. Each of the projections 92 and 94 (FIG. 3) has a first lateral surface 100 and a second lateral surface extending from the surface 82 at third and fourth angle. The first and second lateral surfaces 100 and 102 face downward or outwardly and toward the lateral sides 22 and 24 of the apparatus 10. It is contemplated that the surfaces 96, 98, and the first and second lateral surfaces may extend from the surface 82 at any desired angle. The projections 92 and 94 also include lower surfaces 103 extending generally parallel to the surface 82.

Each of the surfaces 96, 98, 100, and 102 has a trapezoidal shape. The lateral surfaces 100 and 102 intersect the first surface 96 and the second surface 98. It is contemplated that the projections 92 and 94 may have any desired configuration.

An axially extending opening 104 (FIG. 4) extends through the outer surface 82 and the inner surface 84 of the lower retaining member 81. The mounting member 150 extends into the opening 104 to connect the mounting member to the lower retaining member 81. The lower retaining member 81 has a frustoconical surface 106 at least partially defining the opening 104. A lower portion of the opening 104 has a first diameter and an upper portion of the opening has a second diameter smaller than the first diameter. The opening 104 is centrally located between the rails 88. Although the opening 104 is described as being circular, it is contemplated that the opening may have any desired shape.

A flange portion 108 (FIGS. 1 and 3-5) extends from the lower retaining member 81 on the anterior end 20 of the disc 26. The flange portion 108 has a recess 110. The recess 110 is defined by an upper surface 112 and side surfaces 114 and 116 extending downwardly from the upper surface 112. An oval shaped slot 118 extends through the upper surface 112 of the flange portion 108. The slot 118 extends in a direction transverse to the direction in which the rails 88 extend.

The inner concave surface 84 (FIG. 4) of the lower retaining member 81 is affixed or bonded to the resilient core 130. The lower retaining member 81 includes a peripheral flange portion 120 extending toward the upper retaining device 30. The flange 120 encircles the core 130. The flange 120 has a radially inner surface 122 facing the core 130. The surface 122 extends radially outwardly from the concave surface 84 and toward the upper retaining device 30. The surface 122 on the flange 120 is not connected to the core 130. Accordingly, the flange 122 may move relative to the core 130.

It is contemplated that the surface 122 may be spaced from the core 130 until a predetermined load is applied to the apparatus 10. The core 130 may deflect toward the surface 122 on the flange 120 when a load is applied to the apparatus 10 that moves the upper and lower retaining devices 30 and 80 relative to each other. When a predetermined load is applied to the apparatus 10 the core 130 may deflect into engagement with the surface 122 on the flange 120. When the core 130 engages the flange 120, the core stiffens since further deflection of the core is restricted by the flange 120.

The surface 122 of the flange 120 may have any desired configuration. The surface 122 may have a first portion that extends closer to the core 130 than a second portion so that the core engages the first portion of the surface 122 prior to engaging the second portion of the surface 122. Accordingly, the core 130 may engage different portions of the surface 122 as different loads are applied to the apparatus 10 to vary the stiffness of the core at different loads. It is also contemplated that the flange 120 on the lower retaining member 81 may engage the flange 70 on the upper retaining member 31 when a predetermined load is applied to the apparatus 10.

It is contemplated that the retaining member 81 may have an inner surface (not shown) extending from the concave inner surface 84 to the opening 104 and spaced from the core 130 until a predetermined load is applied to the apparatus 10. When the predetermined load is applied to the apparatus 10, the core 130 deflects into engagement with the inner surface (not shown) extending from the concave surface 84 to the opening 104. When the core 130 engages the inner surface extending from the concave surface 84 to the opening 104, the core stiffens since further deflection of the core is restricted by the retaining member 81.

The resilient core 130 is one-piece and may be made of a urethane silicone blend manufactured by the Polymer Technology Group located in Berkley, Calif. The resilient core 130 may be adhered or bonded to the upper and lower retaining members 31 and 81 in any desired manner. It is contemplated that the resilient core 130 could be insert molded, transfer molded or injection molded between the upper and lower retaining members 31 and 81. The core 130 may be molded between the upper and lower retaining members 31 and 81 by injecting the material for the core through one of the openings 56 or 104 in the upper and lower retaining members.

The resilient core 130 may be made of a polymer that is a silicone-polycarbonate-urethane copolymer by the name of CarboSil™ manufactured by the Polymer Technology Group located in Berkley, Calif. The resilient core 130 is prepared through a multi-step bulk synthesis during which polydimethylsiloxane is incorporated into the polymer soft segment with aliphatic, hydroxyl-terminated polycarbonate oligomers. The hard segment consists of an aromatic diisocyanate with a low molecular weight glycol chain extender. The copolymer chains are terminated with silicone.

The material of the resilient core 130 combines the biocompatibility and biostability of silicone elastomers with the processibility and toughness of thermoplastic urethane elastomers. The material of the resilient core 130 has a relatively high hard segment content that softens significantly upon reaching equilibrium with the body of a patient. The relevant equilibrium involves thermal equilibrium with the body at approximately 37° C. and equilibrium water and solute uptake by the polymer after being implanted in the body. The material of the resilient core 130 has a decreased modulus at 37° C. compared to that at room temperature. Accordingly, the higher durometer polymer can be used for its biostability, since conditions in the human body lower the modulus of the polymer to the desired range of compressive stiffness.

The resilient core 130 is wedge shaped. The upper retaining member 31 is spaced from the lower retaining member 81 a first distance adjacent the proximal side 18 of the disc 26. The upper retaining member 31 is spaced from the lower retaining member 81 a second distance greater than the first distance adjacent the anterior side 20 of the disc 26. It is contemplated that the upper retaining member 31 may be spaced from the lower retaining member 81 by any desired distances.

The core 130 has an upper or first convex surface 132. The upper convex surface 132 is affixed to the concave inner surface 34 of the upper retaining member 31. A lower or second convex surface 134 is affixed to the concave inner surface 84 of the lower retaining member 81.

The core 130 includes a radially outer surface 136. Transition surfaces 138 extend between the radially outer surface 136 and the upper and lower surfaces 132 and 134. The radially outer surface 136 may be spaced from the flanges 70 and 120 on the upper and lower retaining members 31 and 81 until the predetermined load is applied to the apparatus 10.

The peripheral surface 136 and the transition surfaces 138 may have any desired configuration. The surfaces 136 and 138 may have first portions that extend closer to the flanges 70 and 120 than second portions so that the first portions engage the flanges prior to the second portions. Accordingly, the different portions of the surfaces 136 and 138 may engage the flanges 70 and 120 as different loads are applied to the apparatus 10 to vary the stiffness of the core 130 at different loads.

Each of the retaining devices 30 and 80 (FIGS. 1-7) includes a mounting member 150 to help connect the disc 26 to the vertebrae 12 and 14. The mounting members 150 may help position the disc 26 between the vertebrae 12 and 14. The mounting members 150 (FIG. 6) extend into the openings 56 and 104 in the retaining members 31 and 81 when the mounting members are connected to the disc 26. The mounting members 150 may be connected to the disc 26 prior to inserting the apparatus 10 between the vertebrae 12 and 14. It is also contemplated that the disc 26 may be inserted between the vertebrae 12 and 14 after the mounting members 150 are connected to the vertebrae. The rails 38 and 88 on opposite sides of the openings 56 and 104 of the disc 26 may engage the mounting members 150 to guide the disc into a desired position between the vertebrae 12 and 14.

A first embodiment of a mounting member 150 is shown in FIGS. 1-4 and 6-8. The mounting members 150 are identical to each other. Accordingly, only one mounting member 150 will be described in detail. The mounting member 150 (FIGS. 6-8) is rigid and made of any desired biocompatible material such as a biocompatible metal or polymer. It is contemplated that the mounting member 150 may be made of a titanium alloy.

The mounting member 150 has a generally circular body 151. It is contemplated that the body 151 of the mounting member 150 may have any desired configuration that permits the mounting member to slide into the openings 56 and 104 in the disc 26. The body 151 of the mounting member 150 has an outer surface 152 that faces the vertebra. An inner concave surface 154 (FIG. 4) of the mounting member 150 faces the resilient core 130. The inner concave surface 154 of the mounting member 150 of the upper retaining device 30 faces the upper surface 132 of the core 130. The inner concave surface 154 of the mounting member 150 of the lower retaining device 80 faces the lower surface 134 of the core 130.

The resilient core 130 (FIGS. 9-10) deflects toward the concave surfaces 154 when a load is applied to the apparatus 10 to move the upper and lower retaining devices 30 and 80 relative to each other. The core 130 deflects into the openings 56 and 104 in the upper and lower retaining members 31 and 81 and into engagement with the concave surfaces 154 when the spine 16 is subject to a predetermined load, as shown in FIG. 10. When the core 130 engages the surfaces 154 of the mounting members 150, the resilient core stiffens since further deflection of the core toward the retaining devices 30 and 80 is restricted. It is contemplated that the mounting member 150 may have an axially extending opening to permit the escape of gas from between the core 130 and the mounting member.

The surfaces 154 of the mounting members 150 may have any desired configuration. The core 130 may engage different portions of the surfaces 154 as different loads are applied to the apparatus 10 to vary the stiffness of the core 130 at different loads. It is also contemplated that the surface 154 of the mounting member 150 of the retaining device 30 may have a different configuration than the surface 154 of the mounting member 150 of the retaining device 80.

A central rail or rib 156 (FIGS. 3 and 6-8) of the mounting member 150 extends from the surface 152 of the body 151 and is engageable with a vertebra. The rib 156 has a length extending from a distal or posterior side of the mounting member 150 toward a proximal or anterior side of the mounting member. Accordingly, the length of the rail or rib 156 extends generally transverse to the first and second ends 18 and 20 and generally parallel to the rails 36 and 38 or 86 and 88 when the mounting member 150 is connected with the retaining member 31 or 81.

The rib 156 includes arcuate lateral surfaces 158 extending from the surface 152. Planar lateral surfaces 160 extend upward from the arcuate surfaces 158. Upper surfaces 162 extend at an angle to the planar surfaces 160. The upper surfaces 162 extend at an angle to each other to form an apex of the rib 156.

A distal or posterior portion 164 (FIGS. 6-8) of the rib 156 tapers from the apex of a central portion 166 of the rib toward the surface 152 of the mounting member 150. The posterior portion 164 includes upper surfaces 168 extending at an angle to each other and at an angle to the planar lateral surfaces 160. The posterior portion 164 of the rib 156 includes a posterior surface 170 that is triangular shaped. A pair of transition surfaces 172 extend between the posterior surface 170, the upper surfaces 168 and the arcuate lateral surfaces 158. The central portion 166 of the rail 156 includes a U-shaped recess 178 for providing bony ingrowth. The recess 178 extends from the apex of the rib 156 to the arcuate surfaces 158.

A pair of transverse rails or ribs 180 extend laterally from the central portion 166 of the rib 156. The rails 180 extend from the surface 152 of the body 151 a distance that is smaller than the distance that the rail 156 extends from the surface 152. Accordingly, the rail 156 may extend into a vertebra further than the ribs 180. Each of the rails 180 has a length extending from the central portion 166 of the rail 156 to a lateral side of the mounting member 150. Accordingly, the lengths of the rails or ribs 180 extend generally transverse to the rails 156, 36, 38, 86 and 88 when the mounting members 150 are connected with the retaining members 31 or 81. The lengths of the rails 180 extend generally perpendicular to the rails 156, 36, 38, 86, and 88 when the mounting members 150 are connected to the retaining members 31 or 81.

Each of the ribs 180 includes arcuate surfaces 182 extending from the surface 152. An anterior surface 184 extends from the arcuate surface 182 and generally perpendicular to the surface 152 of the mounting member 150. A posterior surface 186 extends at an angle to the anterior surface 184.

The body 151 of the mounting member 150 has a radially outer surface 190. A rounded transition surface 192 extends from the radially outer surface 190 to the concave surface 154. The mounting member 150 has a first diameter adjacent the outer surface 190 and a second diameter adjacent the transition surface 192 that is smaller than the first diameter. The radially outer surfaces 190 and/or the transition surfaces 192 of the mounting members 150 may engage the rails 38 and 88 on the retaining members 31 and 81 to guide movement of the disc 26 in a first posterior direction relative to the mounting members and the vertebrae 12 and 14 as the disc is being inserted between the vertebrae.

The radially outer surfaces 190 on the mounting members 150 engage the frustoconical surfaces 57 and 106 on the upper and lower retaining members 31 and 81 when the mounting members are in the openings 56 and 104 in the disc 26. The engagement of the surfaces 190 with the surfaces 57 and 106 creates interference fits between the mounting members 150 and the disc 26. Accordingly, the mounting members 150 are fixedly connected to the disc 26 and the disc is prevented from moving relative to the mounting members.

The radially outer surface 190 has two recesses 196, one of which is shown in FIGS. 6 and 8. The recesses 196 are located at 180° relative to each other. Although the mounting member 190 is described as having two recesses 196, it is contemplated that the mounting member 150 may have any desired number of recesses.

Figure 11:
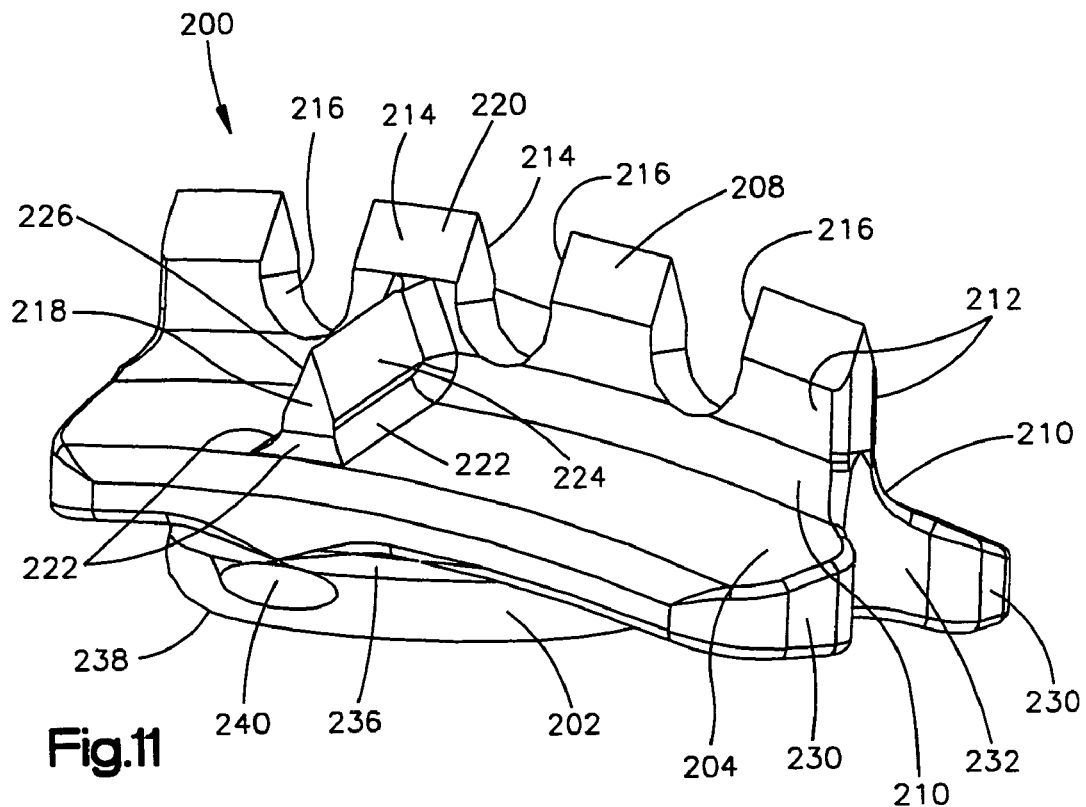
FIG. 11 is a pictorial view of a second embodiment of a mounting member for use with the artificial disc of FIG. 3.
Figure 12:
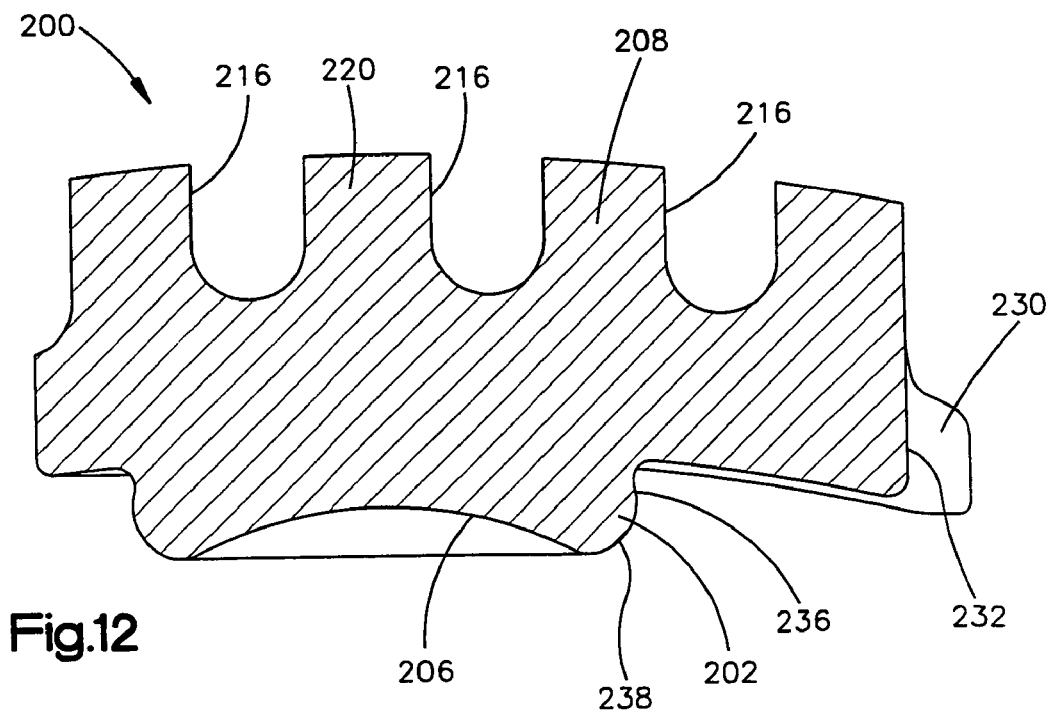
FIG. 12 is a sectional view of the mounting member of FIG. 11.

A second embodiment of a mounting member 200 for use with the disc 26 is illustrated in FIGS. 11 and 12. The mounting member 200 (FIG. 11) is rigid and made of any desired biocompatible material such as a biocompatible metal or polymer. It is contemplated that the mounting member 200 may be made of a titanium alloy. It is also contemplated that mounting members 200 may be formed as one piece with the retaining members 31 and 81.

The mounting member 200 has a generally circular base 202. The base 202 extends into one of the openings 56 and 104 in the disc 26 to connect the mounting member 200 to the disc. It is contemplated that the base 202 may have any desired configuration that permits the base to slide into the openings 56 and 104 in the disc 26.

The mounting member 200 (FIG. 11) has an outer surface 204 that faces a vertebra. An inner concave surface 206 of the mounting member 200 faces the resilient core 130. The inner concave surface 206 of the mounting member 200 of the upper retaining device 30 faces the upper surface 132 of the core 130. The inner concave surface 206 of the mounting member 200 of the lower retaining device 80 faces the lower surface 134 of the core 130.

The resilient core 130 deflects toward the concave surfaces 206 when a load is applied to the apparatus 10 to move the upper and lower retaining devices 30 and 80 relative to each other. The core 130 deflects into the openings 56 and 104 in the upper and lower retaining members 31 and 81 and into engagement with the concave surfaces 206 when the spine 16 is subject to a predetermined load. When the core 130 engages the surfaces 206 of the mounting members 200, the resilient core stiffens since further deflection of the core toward the retaining devices 30 and 80 is restricted. It is contemplated that the mounting member 200 may have an axially extending opening to permit the escape of gas from between the core 130 and the mounting member.

The concave surfaces 206 of the mounting members 200 may have any desired configuration. The core 130 may engage different portions of the surfaces 206 as different loads are applied to the apparatus 10 to vary the stiffness of the core 130 at different loads. It is also contemplated that the surface 206 of the mounting member 200 of the retaining device 30 may have a different configuration than the surface 206 of the mounting member 200 of the retaining device 80.

A central rail or rib 208 of the mounting member 200 extends from the surface 204 and is engageable with a vertebra. The rail 208 has a length extending from a distal or posterior side of the mounting member 200 toward a proximal or anterior side of the mounting member. Accordingly, the length of the rail or rib 208 extends generally transverse to the first and second ends 18 and 20 and generally parallel to the rails 36 and 38 or 86 and 88 when the mounting member 200 is connected with the retaining member 31 or 81.

The rail or rib 208 includes arcuate lateral surfaces 210 extending from the surface 204. Planar lateral surfaces 212 extend upward from the arcuate surfaces 210. Upper surfaces 214 extend at an angle to the planar surfaces 212. The upper surfaces 214 extend at an angle to each other to form an apex of the rib 208.

The rib 208 includes a plurality of U-shaped recess 216 for providing bony ingrowth. The recesses 216 extend from the apex of the rib 208 to the arcuate surfaces 210. Although the mounting member 200 is shown as having three U-shaped recesses 216 it is contemplated that the mounting member may have any desired number of recesses.

A pair of transverse ribs 218, one of which is shown in FIG. 11, extend laterally from a central portion 220 of the rib 208. The ribs 218 extend from the surface 204 a distance that is smaller than the distance that the rib 208 extends from the surface 204. Accordingly, the rib 208 may extend into a vertebra farther than the ribs 218. Each of the rails or ribs 218 has a length extending from the central portion 220 of the rib 208 to a lateral side of the mounting member 200. Accordingly, the lengths of the rails or ribs 218 extend generally transverse to the rails 208, 36, 38, 86 and 88 when the mounting members 200 are connected with the retaining members 31 or 81. The lengths of the rails 218 extend generally perpendicular to the rails 156, 36, 38, 86, and 88 when the mounting members 200 are connected to the retaining members 31 or 81.

Each of the ribs 218 includes arcuate surfaces 222 extending from the surface 204. An anterior surface 224 extends from the arcuate surface 222. A posterior surface 226 extends from the arcuate surface 222. The posterior surface 226 also extends at an angle to the anterior surface 224.

Flanges 230 extend from an anterior side of the mounting member 200. The flanges 230 extend from opposite lateral sides of the rib 208. The flanges 230 define a recess 232 in the anterior side of the mounting member 200.

The base 202 (FIGS. 11 and 12) has a radially outer surface 236. A rounded transition surface 238 extends from the radially outer surface 236 to the concave surface 206. The base 202 has a first diameter adjacent the outer surface 236 and a second diameter adjacent the transition surface 238 that is smaller than the first diameter. The radially outer surfaces 236 and/or the transition surfaces 238 of the mounting members 200 may engage the rails 38 and 88 on the retaining members 31 and 81 to guide movement of the disc 26 in a first posterior direction relative to the mounting members and the vertebrae 12 and 14 as the disc is being inserted between the vertebrae.

The radially outer surfaces 236 on the mounting members 200 engage the frustoconical surfaces 57 and 106 on the upper and lower retaining members 31 and 81 when the mounting members are in the openings 56 and 104 in the disc 26. The engagement of the surfaces 236 with the surfaces 57 and 106 creates interference fits between the mounting members 200 and the disc 26. Accordingly, the mounting members 200 are fixedly connected to the disc 26 and the disc is prevented from moving relative to the mounting members.

The radially outer surface 236 has two recesses 240, one of which is shown in FIG. 11. The recesses 240 are located at 180° relative to each other. Although the mounting member 200 is described as having two recesses 240, it is contemplated that the mounting member 200 may have any number of recesses.

Figure 13:
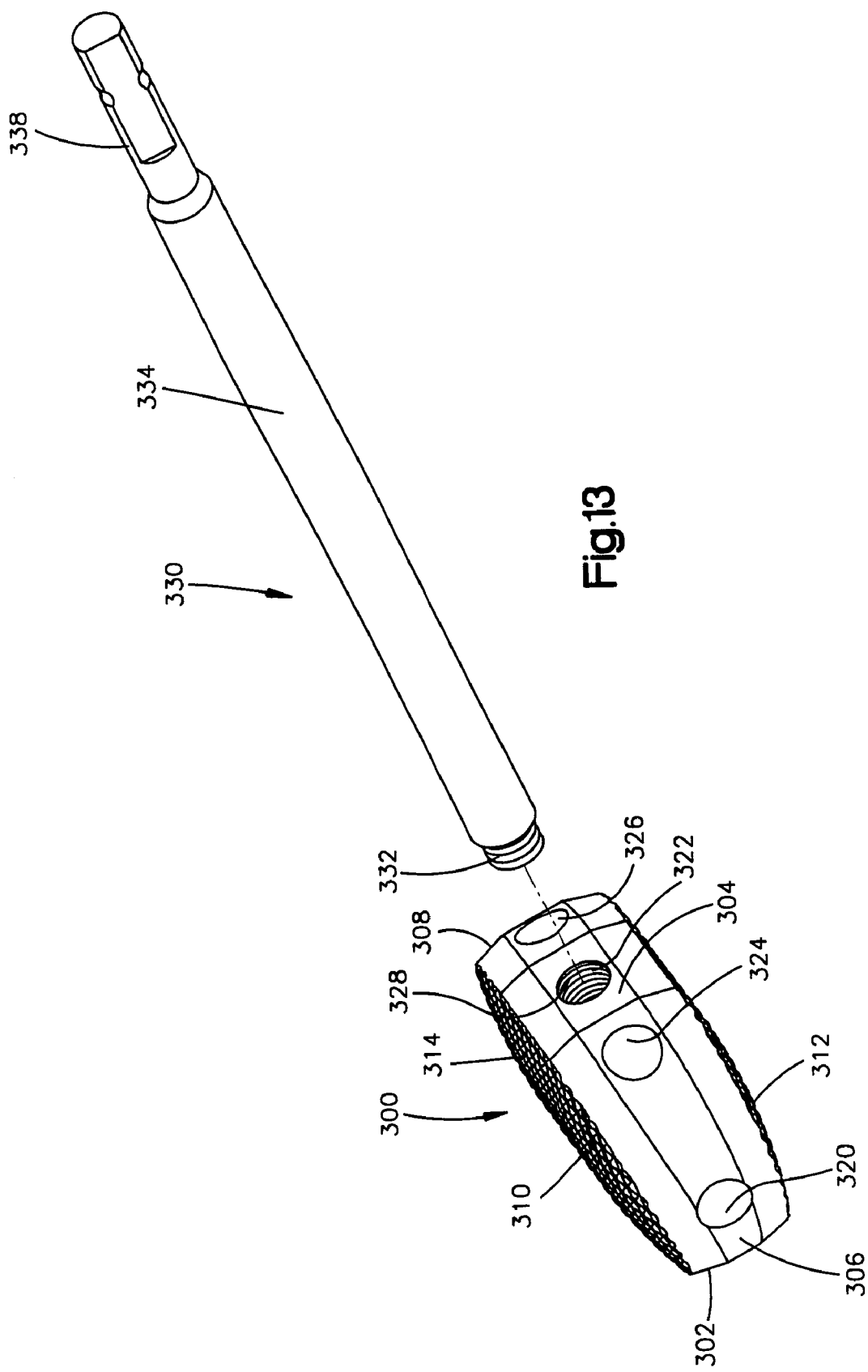
FIG. 13 is a pictorial view of a trial sizer and an insertion handle for use in determining the appropriate sized apparatus of FIG. 1 for insertion between adjacent vertebrae.
Figure 14:
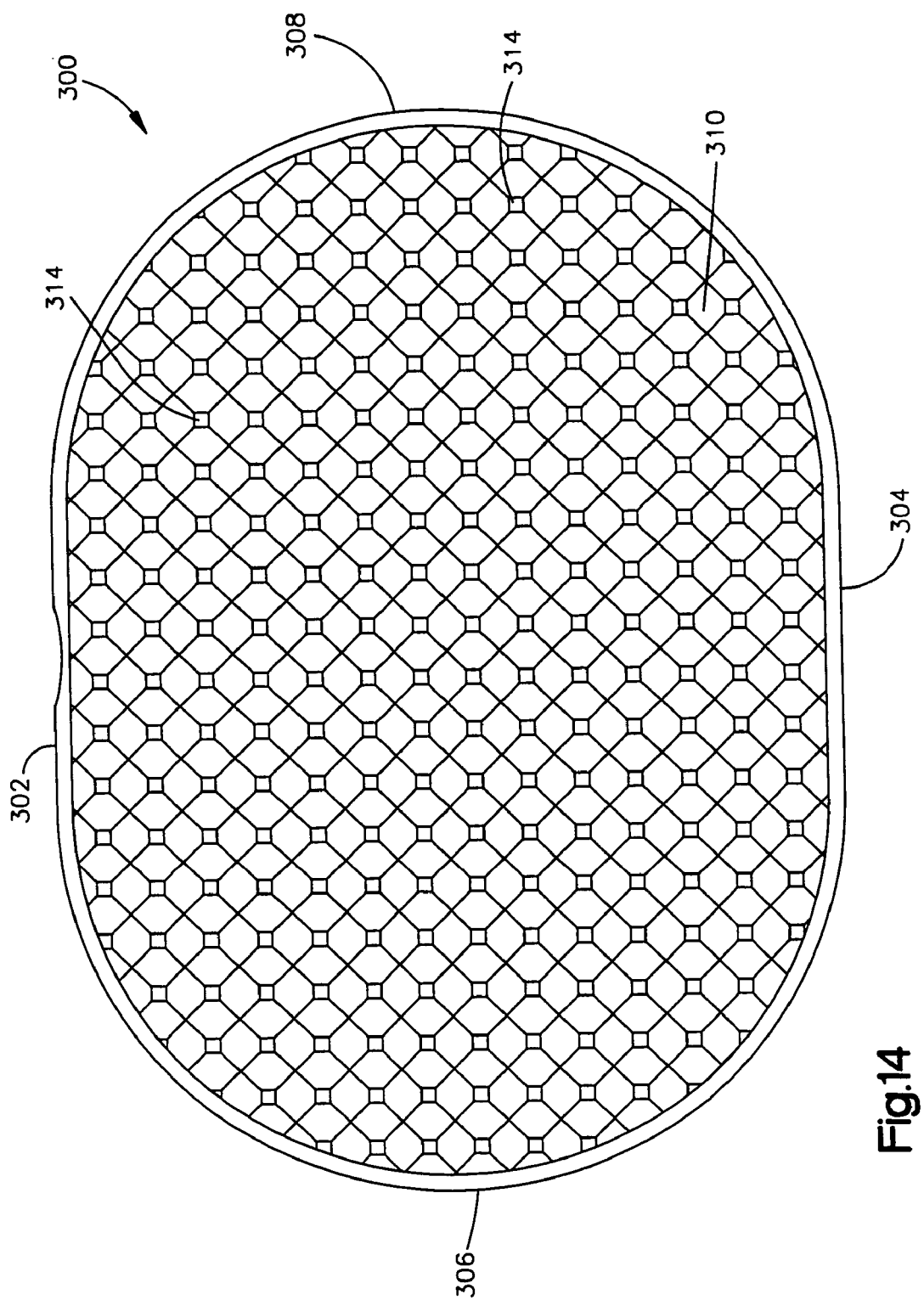
FIG. 14 is a schematic top view of the trial sizer of FIG. 13.

Prior to insertion of the apparatus 10 between the vertebrae 12 and 14, a trial sizer or spacer 300 (FIGS. 13 and 14) is inserted between the vertebrae. The trial sizer or spacer 300 is used to determine a desired position, footprint, wedge angle, and disc height for the apparatus 10. The trial sizer 300 is also used to determine a desired position for the apparatus 10 between the vertebrae. Once the desired position for the apparatus 10 is determined using the trial sizer or spacer 300, the trial sizer may be used to determine a reference point on the spinal column for use in guiding insertion of surgical tools between the vertebrae 12 and 14. Different trial sizers 300 may be inserted and removed from between the vertebrae 12 and 14 until a trial sizer having a desired footprint, wedge angle, and disc height is positioned between the vertebrae. Once the trial sizer 300 having the desired footprint, wedge angle, and disc height is inserted, the size and shape of the apparatus 10 may be determined.

The trial sizer 300 has a shape similar to the apparatus 10 and may be wedge shaped. The trial sizer 300 has first, distal or posterior end 302 and an opposite, second, proximal or anterior end 304. The trial sizer 300 also includes first and second lateral sides 306 and 308 extending between the first and second ends 302 and 304. An upper surface 310 of the trial sizer 300 is engageable with the vertebra 12 and a lower surface 312 is engageable with the vertebra 14. The upper and lower surfaces 310 and 312 have a plurality of projections 314 for engaging the vertebrae 12 and 14. The projections 314 may have any desired configuration.

The trial sizer 300 (FIG. 13) includes a cylindrical passage 320 extending between the first and second lateral sides 306 and 308. The trial sizer 300 includes a central cylindrical passage 322 extending between the first and second ends 302 and 304. The passage 322 bifurcates the wedge angle of the trial sizer 300. The sizer 300 also includes two lateral cylindrical passages 324 and 326 extending between the first and second ends 302 and 304. The passages 322, 324, and 326 extend generally parallel to each other. The passages 322, 324, and 326 intersect the passage 320. It is contemplated that the passages 320, 322, 324, and 326 may have any desired configuration. The passages 320, 322, 324, and 326 can be viewed using desired imaging systems, such as fluoroscopy, to determine if the trial sizer 300 is properly positioned between the vertebrae 12 and 14. When the trial sizer 300 is properly positioned between the vertebrae 12 and 14, the passages 320, 322, 324, and 326 may appear as circles in an image produced by the imaging system. The passages 320, 322, 324, and 326 may appear as ovals in an image when the trial sizer is not properly positioned. The passage 322 has a threaded portion 328 located adjacent the anterior side 304.

An insertion rod 330 is threadably engageable with the threaded portion 328 of the passage 322. The insertion rod 330 may be used for inserting the trial sizer 300 between the vertebrae 12 and 14. The insertion rod 330 may be struck with a mallet or hammer to cause the sizer 300 to move between the vertebrae 12 and 14. The insertion rod 330 has a first or distal threaded end portion 332 that threadably engages the threaded portion 328 of the passage 322. The first threaded end portion 332 has a first diameter. A central portion 334 has a second diameter larger than the first diameter. A radially extending surface (not shown) extends between the first end portion 332 and the central portion 334. The radially extending surface is engageable with the trial sizer 300 to prevent further insertion of the insertion rod 330 into the trial sizer. A second end portion 338 of the insertion rod 330 is connectable with a handle (not shown) in any desired manner.

Figure 15:
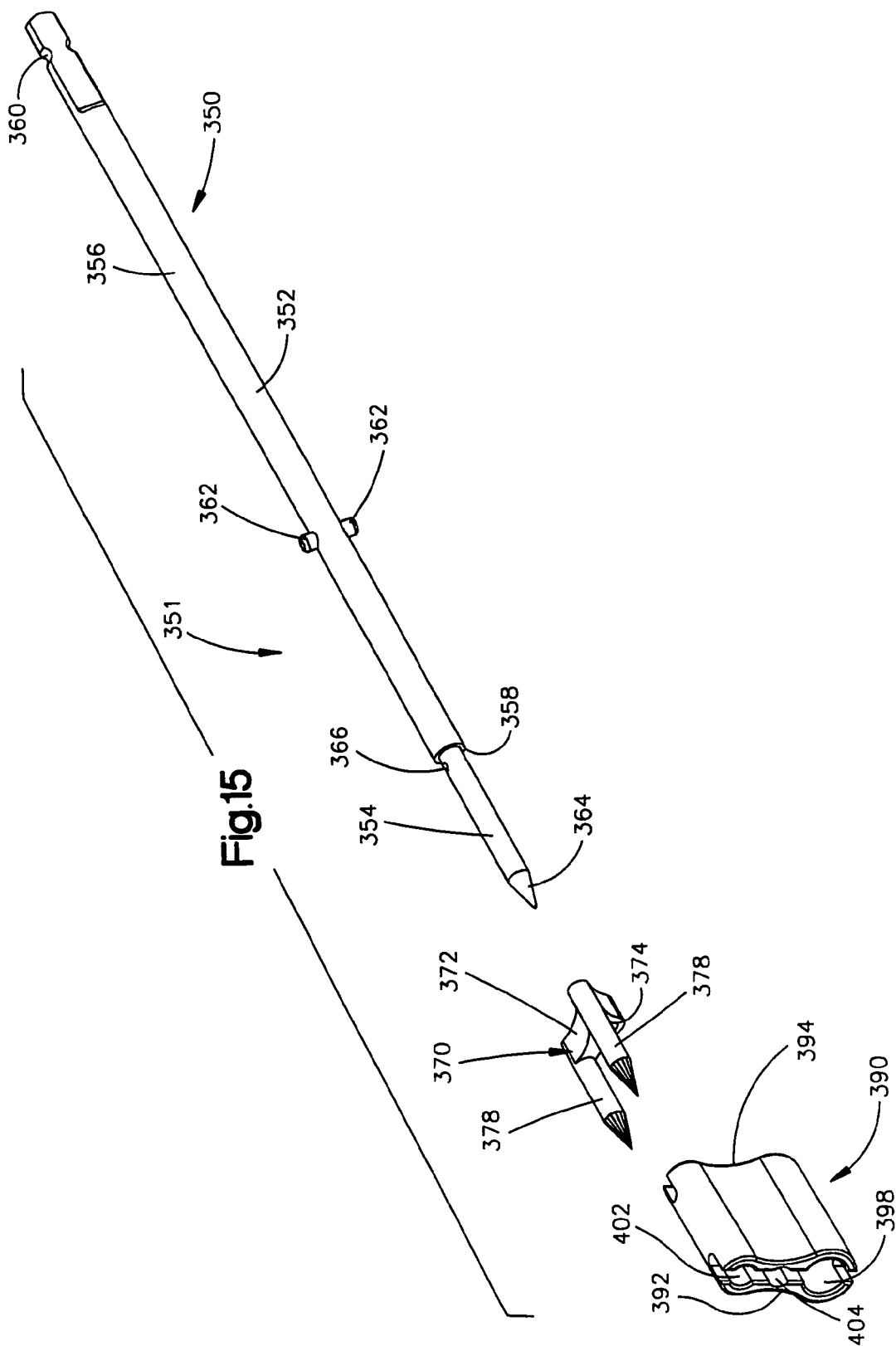
FIG. 15 is an exploded view of a first embodiment of a guide assembly for use in preparing adjacent vertebrae for insertion of the apparatus of FIG. 1.
Figure 16:
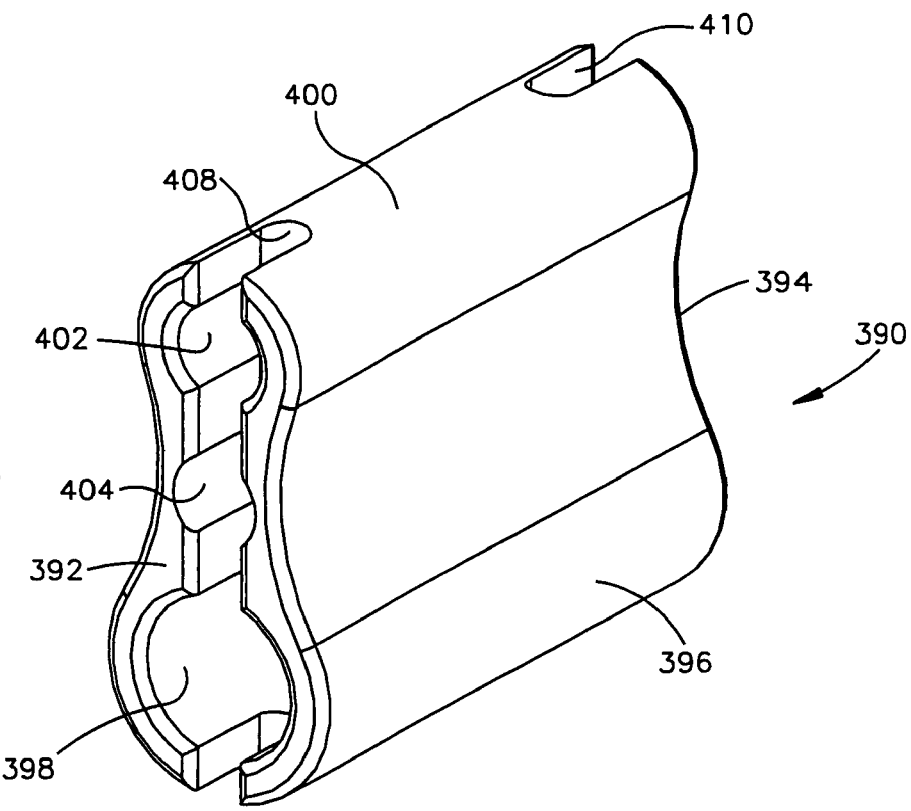
FIG. 16 is a pictorial view of a guide mechanism of the guide assembly of FIG. 15.

After the trial sizer 300 is positioned between the vertebrae 12 and 14 a marker 350 (FIG. 15) of a first embodiment of a guide assembly 351 is connected with any desired vertebra of the spinal column, such as one of the vertebrae 12 and 14. The marker 350 is connected to one of the vertebrae 12 and 14 at a desired reference point on the desired vertebra, such as the midline of the spine 16. The marker 350 includes a shaft 352 having a first end portion 354 with a first diameter. A central portion 356 of the shaft 352 has a second diameter larger than the first diameter. A radial extending surface 358 extends from the first end portion 354 to the central portion 356. A second end portion 360 of the shaft 352 is connectable with a handle (not shown) in any desired manner.

The central portion 356 includes a pair of radially extending positioning members 362. The positioning members 362 are diametrically opposed. The first end portion 354 has a pointed end 364 for insertion into one of the vertebrae 12 and 14. The end portion 354 also includes a diametrically extending opening 366 located adjacent the radially extending surface 358. The opening 366 receives a pin (not shown) to connect a stabilizing member 370 to the shaft 352.

The stabilizing member 370 includes a body 372 with an axially extending opening 374. A radially extending opening (not shown) in the body 372 intersects the axially extending opening 374. The first end portion 354 of the shaft 352 extends through the opening 374 so that the shoulder 358 engages the body 372. The pin (not shown) extends through the radially extending opening (not shown) in the body 372 and into the opening 366 in the shaft 352 to connect the shaft to the stabilizing member 370 the shaft 352 may be connected to the stabilizing member 370 in any desired manner, such as by welding.

The stabilizing member 370 includes a pair of stabilizing shafts 378 extending from the body 372. The stabilizing shafts 378 extend from the body 372 so that the stabilizing shafts and the shaft 352 form a trident when the shaft 352 is connected with the stabilizing member 370. The stabilizing shafts 378 are inserted into one of the vertebrae 12 and 14 to help retain the marker 350 in the vertebra.

Figure 17:
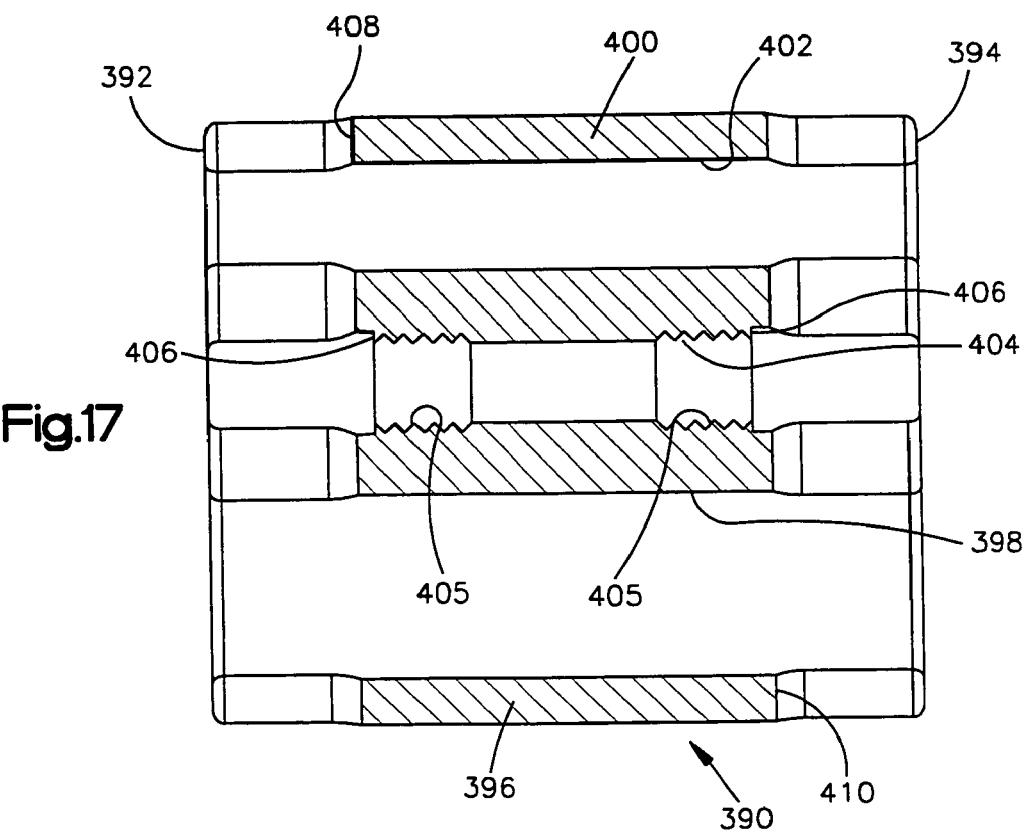
FIG. 17 is a schematic sectional view of the guide member of FIG. 16.

A guide mechanism or member 390 (FIGS. 15 and 17) is used to connect the marker 350 to one of the vertebrae 12 and 14 at the desired reference point. The guide mechanism or member 390 has opposite end portions 392 and 394. A first or lower portion 396 of the guide mechanism or member 390 has a passage 398 having a first diameter. The diameter of the passage 398 is a little larger than the diameter of the insertion rod 330. A second or upper portion 400 has a passage 402 having a second diameter smaller than the first diameter. The diameter of the passage 402 is a little larger than the diameter of the central portion 356 of the shaft 352 of the marker 350.

A central passage 404 extends through the guide member 390 and is located between the passages 398 and 402. The passages 398, 402, and 404 extend generally parallel to each other between the opposite end portions 392 and 394.

The central passage 404 includes threaded portions 405 for threadably engaging a handle (not shown). The guide mechanism 390 includes shoulders 406 partially defining the passage 404. The handle (not shown) includes a shoulder engageable with one of the shoulders 406. The handle is used for handling the guide mechanism 390 and may be connected with the guide mechanism in any desired manner.

The end portion 392 of the guide mechanism 390 includes a recess 408. The end portion 394 includes a recess 410. The recesses 408 and 410 intersect the passages 398, 402, and 404 and extend from the lower portion 396 to the upper portion 400. The recesses 408 and 410 may receive the radially extending positioning members 362 on the shaft 352. Accordingly, the first and second end portions 392 and 394 are substantially similar.

The shaft 352 of the marker 350 is inserted through the passage 402 in the guide mechanism 390 until the radially extending positioning members 362 on the shaft are received in the recess 408. The handle (not shown) may be threadably connected to one of the threaded portions 405. The guide mechanism 390 is then telescoped over the insertion rod 330 extending from the trial sizer 300 when the sizer is between the vertebrae 12 and 14 so that the insertion rod extends into the passage 398 in the guide mechanism. As the guide mechanism 390 is moved axially relative to the insertion rod 330, the first end portion 354 of the shaft 352 is inserted into one of the vertebrae 12 and 14, such as the vertebra 12, at the desired reference point. The stabilizing shafts 378 of the stabilizing member 370 are also inserted into the one vertebra. The shaft 352 of the marker 350 extends parallel to the insertion rod 330. After the marker 350 is connected to one of the vertebrae 12 and 14, the guide member 390 is removed from the marker and the trial sizer 300 is removed from between the vertebrae 12 and 14.

A plurality of guide mechanisms 390 may be provided during surgery. Each guide mechanism 390 would have a different spacing between the passages 398 and 402. Accordingly, a surgeon may choose an appropriate guide mechanism 390 for inserting the marker 350 at the desired reference point on the desired vertebra of the spinal column 16.

After the marker 350 is connected to the desired vertebra of the spinal column 16 and the trial sizer 300 is removed from between the vertebrae 12 and 14, the vertebrae may be cut to receive the apparatus 10. A first cutter 450 (FIGS. 18-20) may be inserted between the vertebrae 12 and 14 to cut grooves into the vertebrae for receiving the rails 36, 38, 86, and 88 on the apparatus 10. The first cutter 450 has a shape similar to the apparatus 10 and may be wedge shaped. The first cutter 450 has a first, distal or posterior end 452 and an opposite, second, proximal or anterior end 454. The cutter 450 also includes first and second lateral sides 456 and 458 extending between the first and second ends 452 and 454. An upper surface 460 of the cutter 450 may engage the vertebra 12 and a lower surface 462 may engage the vertebra 14.

A plurality of rows 464 of teeth 466 extend from the upper and lower surfaces 460 and 462 adjacent the lateral sides 456 and 458. The teeth 466 cut grooves in the vertebrae 12 and 14 for receiving the ribs 36 and 86 of the apparatus 10. A plurality of rows 467 of teeth 468 extend from the upper and lower surfaces 460 and 462 adjacent a central portion of the cutter 450. The teeth 468 cut grooves in the vertebrae 12 and 14 for receiving the ribs 38 and 88 of the apparatus 10. The rows 467 of teeth 468 extend from the upper and lower surfaces 460 and 462 a distance smaller than the distance that the rows 464 of teeth 466 extend from the upper and lower surfaces. Accordingly, the rows 464 of teeth 466 may cut deeper grooves into the vertebrae 12 and 14 than the rows 467 of teeth 468. The rows 464 and 467 of teeth 466 and 468 extend from the second end 454 toward the first end 452 a first distance that is approximately equal to half the distance between the first and second ends of the cutter 450.

The cutter 450 includes a cylindrical passage 470 extending between the first and second lateral sides 456 and 458. The cutter 450 includes a central cylindrical passage 472 extending between first and second ends 452 and 454. The cutter 450 also includes two lateral cylindrical passages 474 and 476 extending between the first and second ends 452 and 454. The passages 472, 474, and 476 extend generally parallel to each other. The passages 472, 474, and 476 intersect the passage 470. It is contemplated that the passages 470, 472, 474, and 476 may have any desired configuration. The passages 470, 472, 474, and 476 may be viewed using an imaging system, such as fluoroscopy, to determine if the cutter 450 is properly positioned between the vertebrae 12 and 14. When the cutter 450 is properly positioned between the vertebrae 12 and 14, the passages 470, 472, 474, and 476 may appear as circles in an image produced by the imaging system. The passages 470, 472, 474, and 476 may appear as ovals in an image when the cutter 450 is not properly positioned. The passage 472 has a threaded portion 478 located adjacent the anterior side 454.

The insertion rod 330 may threadably engage the threaded portion 478 of the passage 472. The insertion rod 330 may be used for inserting the cutter 450 between the vertebrae 12 and 14. The insertion rod 330 is inserted into the passage 398 in the guide member 390. The guide member 390 is then telescoped over the shaft 352 of the marker 350 until the recess 408 receives the radially extending positioning members 362 on the shaft 352. Accordingly, the cutter 450 is in a desired alignment with the vertebrae 12 and 14. The insertion rod 330 may be struck with a mallet or hammer to cause the cutter 450 to move between the vertebrae 12 and 14 and the teeth 466 and 468 to cut grooves in the vertebrae 12 and 14.

After the cutter 450 has cut grooves in the vertebrae 12 and 14, the cutter 450 is removed from between the vertebrae and the guide member 390 is removed from the marker 350. A second cutter 490 (FIGS. 21-22) may be inserted between the vertebrae 12 and 14 to further cut the grooves into the vertebrae for receiving the ribs 36, 38, 86, and 88 on the apparatus 10. The second cutter 490 is substantially similar to the first cutter 450. The second cutter 490 has a shape similar to the apparatus 10 and may be wedge shaped. The second cutter 490 has a first, distal or posterior end 492 and an opposite, second, proximal or anterior end 494. The cutter 490 also includes first and second lateral sides 496 and 498. An upper surface 500 of the cutter 490 may engage the vertebra 12 and a lower surface 502 may engage the vertebra 14.

A plurality of rows 504 of teeth 506 extend from the upper and lower surfaces 500 and 502 adjacent the lateral sides 496 and 498. The teeth 506 cut grooves in the vertebrae 12 and 14 for receiving the ribs 36 and 86 of the apparatus 10. A plurality of rows 507 of teeth 508 extend from the upper and lower surfaces 500 and 502 adjacent a central portion of the cutter 490. The teeth 508 cut grooves in the vertebrae 12 and 14 for receiving the ribs 38 and 88 of the apparatus 10. The rows 507 of teeth 508 extend from the upper and lower surfaces 500 and 502 a distance smaller than the distance that the rows 504 of teeth 506 extend from the upper and lower surfaces. Accordingly, the rows 504 of teeth 506 may cut deeper grooves into the vertebrae 12 and 14 than the rows 507 of teeth 508. The rows 504 and 507 of teeth 506 and 508 extend from the second end 494 toward the first end 492 a second distance that is greater than half the distance between the posterior and anterior sides 492 and 494. Accordingly, the rows 504 and 507 of teeth 506 and 508 extend a distance greater that the first distance that that the rows 464 and 467 of teeth 466 and 468 on the first cutter 450 extend.

The cutter 490 includes a cylindrical passage 510 extending between the first and second lateral sides 496 and 498. The cutter 490 includes a central cylindrical passage 512 extending between the first and second ends 492 and 494. The cutter 490 also includes two lateral cylindrical passages 514 and 516 extending between the first and second ends 492 and 494. The passages 512, 514, and 516 extend generally parallel to each other. The passages 512, 514, and 516 intersect the passage 510. It is contemplated that the passages 510, 512, 514, and 516 may have any desired configuration. The passages 510, 512, 514, and 516 may be viewed using an imaging system, such as fluoroscopy, to determine if the cutter 490 is properly positioned between the vertebrae 12 and 14. When the cutter 490 is properly positioned between the vertebrae 12 and 14, the passages 510, 512, 514, and 516 may appear as circles in an image produced by the imaging system. The passages 510, 512, 514, and 516 may appear as ovals in an image when the cutter 490 is not properly positioned. The passage 512 has a threaded portion 518 located adjacent the anterior side 494.

The insertion rod 330 may threadably engage the threaded portion 518 of the passage 512. The insertion rod 330 may be used for inserting the cutter 490 between the vertebrae 12 and 14. The insertion rod 330 is inserted into the passage 398 in the guide mechanism 390. The guide mechanism 390 is then telescoped over the shaft 352 of the marker 350 until the recess 408 receives the radially extending positioning members 362 on the shaft 352. Accordingly, the cutter 490 is in a desired alignment with the vertebrae 12 and 14. The insertion rod 330 may be struck with a mallet or hammer to cause the cutter 490 to move between the vertebrae 12 and 14 and the teeth 506 and 508 to cut grooves in the vertebrae 12 and 14.

An insertion tool 550 (FIGS. 24-25) for inserting the apparatus 10 between the vertebrae 12 and 14 or for inserting the disc 26 between the vertebrae after the mounting members 150 are connected to the vertebrae 12 and 14 is illustrated in FIGS. 24 and 25. The tool 550 (FIG. 24) resembles a common pair of scissors and has a pair of legs 552 and 554 pivotally connected to one another. The tool 550 includes a grasping end 556 formed by a pair of jaws 558 on the legs 552 and 554. The jaws 558 (FIG. 25) include oval shaped projections 560 extending toward each other. The projections 560 are inserted into the openings 68 and 118 in the disc 26 to grasp the disc for insertion between the vertebrae 12 and 14.

The leg 552 (FIG. 24) has an enlarged end 562 opposite the jaw 558. The enlarged end 562 may be struck with a mallet to drive the disc 26 between the vertebrae 12 and 14 if needed. The leg 554 has a curved handle 564 opposite the jaw 558. The handle 564 is easily grasped by a surgeon for manipulating the tool 550.

A locking mechanism 570 prevents the jaws 558 from pivoting away from each other after the projections 560 have been inserted into the openings 68 and 118 in the disc 26. The locking mechanism 570 includes a rod 572 pivotally connected to a mounting portion 574 extending from the leg 554. The rod 572 has a threaded end 576 that extends through an opening 578 in the leg 552. A nut 582 threadably engages the end 576 of the rod 572 and engages the leg 552 to prevent the jaws 558 from pivoting away from each other.

Figure 26:
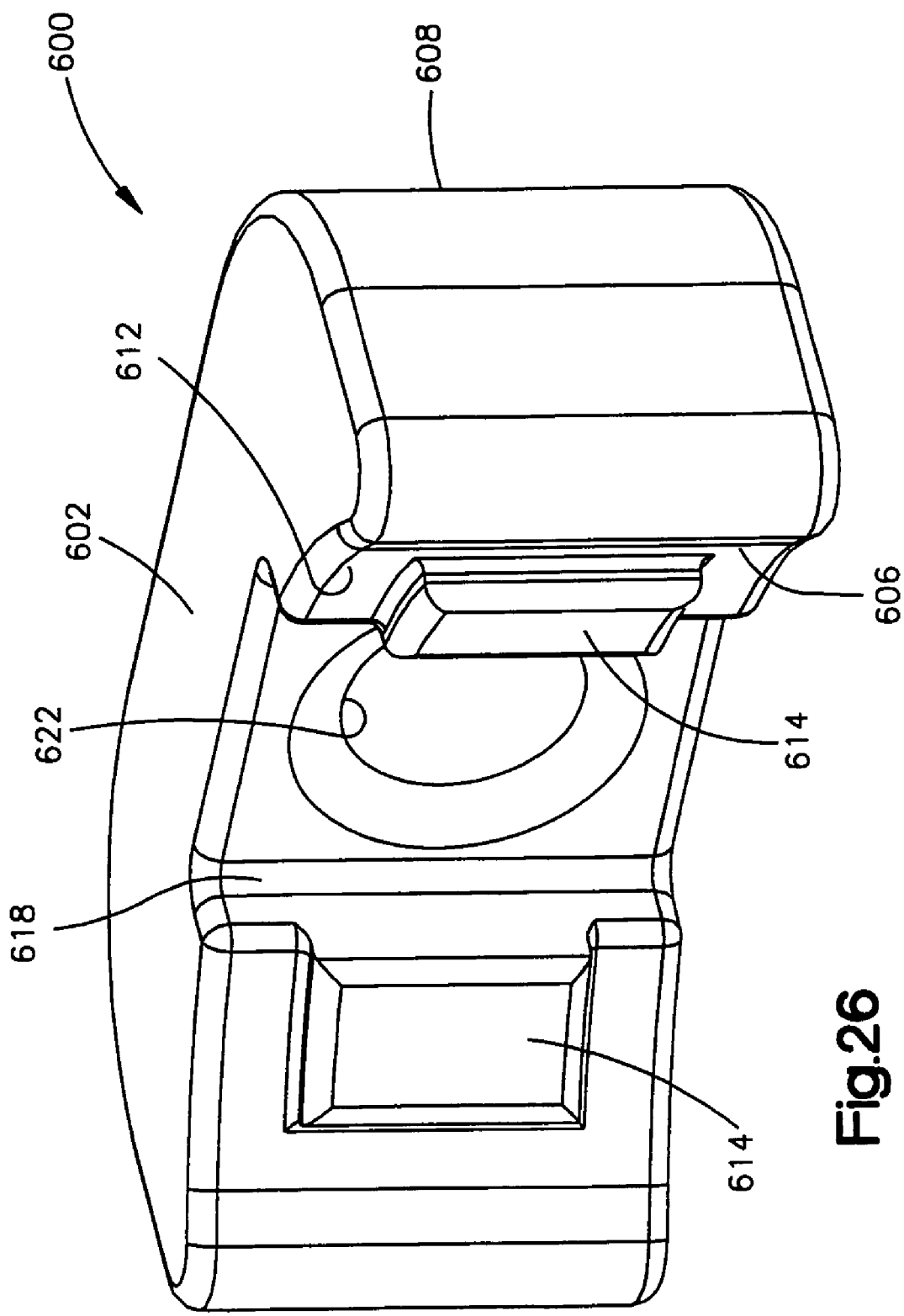
FIG. 26 is a pictorial view of a tamping member for use in inserting the apparatus of FIG. 1 between adjacent vertebrae.

After the apparatus 10 has been inserted between the vertebrae 12 and 14 with the insertion tool 550, a tamping member 600 (FIG. 26) may be used to further position the apparatus between the vertebrae 12 and 14. The tamping member 600 includes a body 602. A first or posterior side 606 of the tamping member 600 is engageable with the second end 20 of the apparatus 10. A second or anterior side 608 of the member 600 faces away from the apparatus 10.

The first side 606 of the member 600 has a contour that matches the contour of the anterior end 20 of the apparatus 10. The posterior side 606 has an arcuate surface 612 that is engageable with the upper and lower retaining members 31 and 81. Rectangular projections 614 extend from the arcuate surface 612. The projections 614 extend between the upper and lower retaining members 31 and 81 to help position the member 600 on the apparatus 10. A recess 618 is centrally located in the arcuate surface 612 between the projections 614. The recess 618 receives the flange portions 58 and 108 on the retaining members 31 and 81. An opening 622 extends through the member 600 and intersects the recess 618. The opening 622 may be threaded to threadably engage a member, such as the insertion rod 330.

The member 600 is placed in engagement with the apparatus 10 so that the arcuate surface 612 engages the upper and lower retaining members 31 and 81 and the projections 614 extend between the upper and lower retaining members 31 and 81. The insertion rod 330 may be struck with a mallet or hammer to further position the apparatus 10 between the vertebrae 12 and 14 after the apparatus 10 has been initially positioned between the vertebrae.

When the apparatus 10 is to be inserted between the vertebrae 12 and 14, an anterior space adjacent the vertebrae is exposed using a retroperitoneal or transperitoneal approach. The space between the vertebrae 12 and 14 is distracted and the disc between the vertebrae is excised. After the disc is excised, the cartilaginous end plates may be removed from the vertebrae 12 and 14. The vertebrae 12 and 14 may be sculpted as desired. The appropriate size apparatus 10 is determined by using trial sizers 300. The trial sizers 300 are inserted between the vertebrae 12 and 14 to determine the desired footprint, wedge angle, and disc height needed to replace the excised disc. The desired footprint, wedge angle and disc height are confirmed using fluoroscopy to determine if the passages 320, 322, 324, and 326 in the trial sizer 300 extend in the desired directions.

The marker 350 is connected with one of the vertebrae 12 and 14 using the trial sizer 300. A midline reference is established using the trial sizer 300. The marker 350 is connected with the vertebra to maintain a reference point to the midline of spinal column 16.

The grooves may be cut into the vertebrae 12 and 14 using the first and second cutters 450 and 490. The cutters 450 and 490 are sequentially inserted between the vertebrae 12 and 14 using the guide assembly 151. The appropriate sized guide mechanism 390 may be used. Accordingly, the cutters 450 and 490 may cut grooves into the vertebrae 12 and 14 at the desired locations. It is contemplated that only one of the cutters 450 and 490 may be used. It is also contemplated that the cutters 450 and 490 may not be used.

After the grooves have been cut into the vertebrae 12 and 14, the cutters 450 and 490 are removed from between the vertebrae and the marker 150 may be removed from the vertebra 12. The insertion tool 550 is connected with the apparatus 10. The apparatus 10 is then inserted between the vertebrae 12 and 14. During insertion of the apparatus 10, the ribs 156 and 180 on the mounting members 150 or the ribs 208 and 218 on the mounting members 200 cut into the vertebrae 12 and 14.

It is contemplated that the mounting members 150 or 200 may be connected to the vertebrae 12 and 14 before the disc 26 is inserted between the vertebrae. The surfaces 190 and 192 on the mounting members 150 or the surfaces 236 and 238 on the mounting members 200 may guide insertion of the disc 26. The ribs 38 and 88 on the disc 26 may guide insertion of the mounting members 150 or 200 into the openings 56 and 104 in the disc 26.

After the disc 26 is placed into the desired position between the vertebrae 12 and 14, the tool 550 is removed from the disc. The tamping member 600 may be positioned with the arcuate surface 612 in engagement with the retaining members 31 and 81 and the projections 614 between the retaining members. The insertion rod 330 may be struck with a mallet or hammer to further position the apparatus 10 relative to the vertebrae 12 and 14.

The ribs 36, 38, 86 and 88 on the disc 26 engage the vertebrae 12 and 14 when the mounting members 150 or 200 are inserted in the openings 56 and 104 in the disc 26. The mounting members 150 or 200 and ribs 36, 38, 86 and 88 retain the apparatus 10 in position between the vertebrae 12 and 14.

When the apparatus 10 is in use in the spinal column 16, the upper retaining device 30 is affixed to the vertebra 12. The ribs 36 and 38 and the ribs 156 and 180 on the mounting member 150 or the ribs 208 and 218 on the mounting member 200 resist relative movement between the upper retaining device 30 and vertebra 12. The lower retaining device 80 is affixed to the vertebra 14. The ribs 86 and 88 and the ribs 156 and 180 on the mounting member 150 or the ribs 208 and 218 on the mounting member 200 resist relative movement between the lower retaining device 80 and the vertebra 14.

When the upper and lower retaining devices 30 and 80 move relative to each other, such as when the spine 16 is in compression, as shown in FIG. 10, the resilient core 130 deflects toward the concave surfaces 154 on the mounting members 150 or the concave surfaces 206 on the mounting members 200. Accordingly, the core 130 expends energy to reduce stress in the core upon relative movement between the upper and lower retaining devices 30 and 80 to provide a relatively long fatigue life for the apparatus 10. The resilient core 130 may deflect into engagement with the surfaces 154 of the mounting members 150 or the surfaces 206 of the mounting members 200 when a predetermined load is applied. Accordingly, the core 130 stiffens when the core engages the surfaces 154 or 206 since further deflection of the core is restricted.

It is contemplated that the disc 26 may be inserted between the vertebrae 12 and 14 without use of the mounting members 150 or 200. If the disc 26 is used without the mounting members 150 or 200, it is contemplated that the retaining members 31 and 81 of the retaining devices 30 and 80 would include inner concave surfaces similar to the inner concave surfaces 154 of the mounting members 150. The core 130 would be spaced from the inner concave surfaces on the retaining members 31 and 81 and deflect into engagement with the inner concave surfaces when a predetermined load was applied to the apparatus 10.

Figure 27:
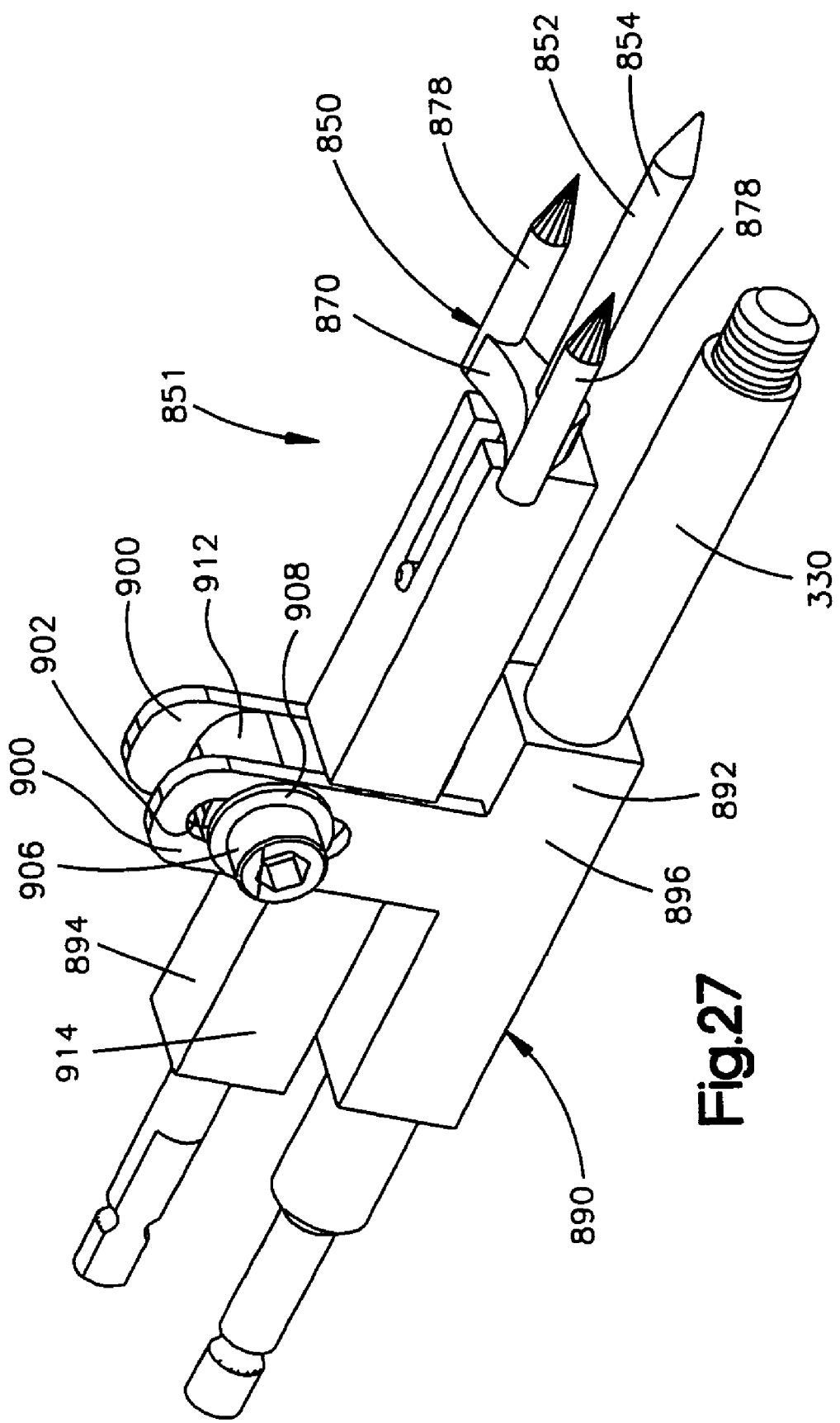
FIG. 27 is a pictorial view of second embodiment of a guide assembly for use in preparing adjacent vertebrae for insertion of the apparatus of FIG. 1.
Figure 28:
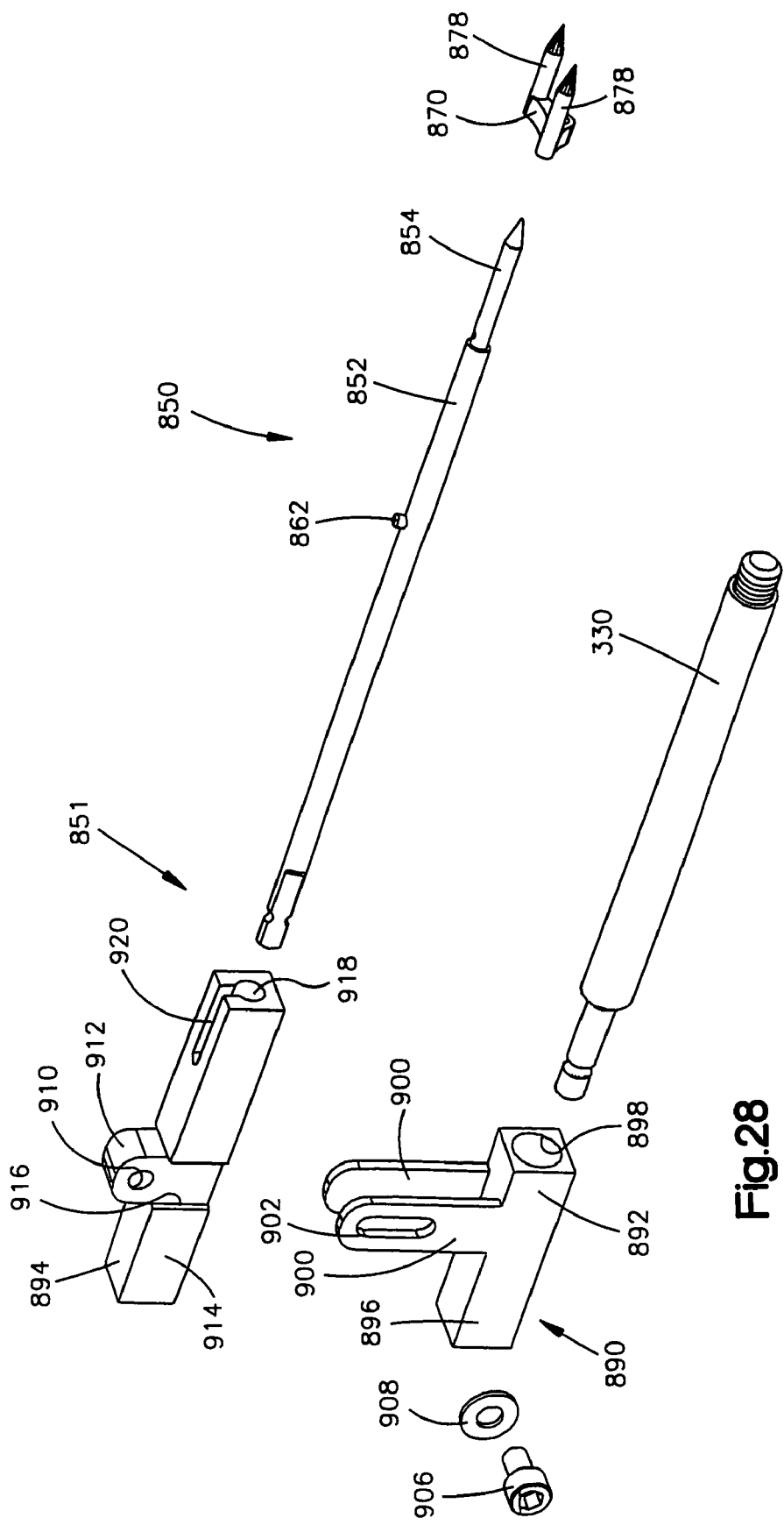
FIG. 28 is an exploded view of the guide assembly of FIG. 27.
Figure 29:
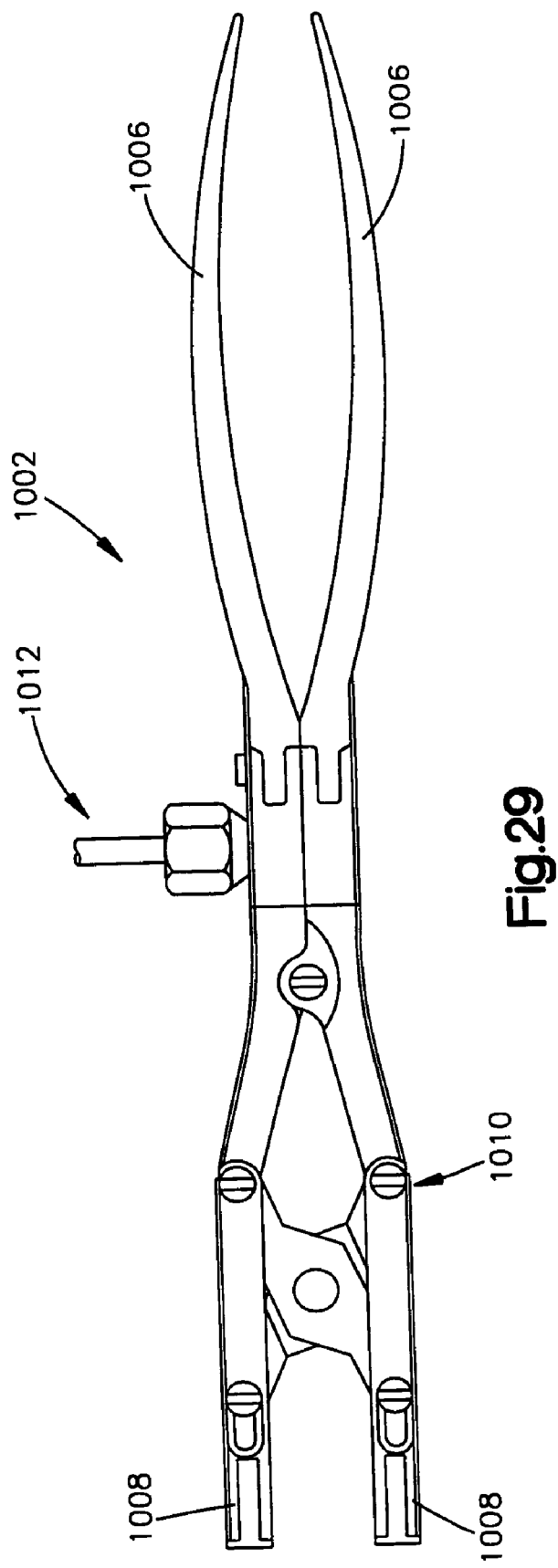
FIG. 29 is a schematic side view of an actuator for use in connecting mounting members shown in FIGS. 6 and 11 to adjacent vertebrae.

A second embodiment of a guide assembly 851 is illustrated in FIGS. 27-28. The guide assembly 851 includes a marker 850 having a shaft 852 and a stabilizing member 870 that are substantially similar to the shaft 352 and the stabilizing member 370 of the guide assembly 351. Accordingly, the shaft 852 and stabilizing member 870 will not be described in detail.

A guide mechanism 890 is used to connect the marker 850 to one of the vertebrae 12 and 14. The guide mechanism 890 includes a first or lower guide portion or member 892 and a second or upper guide portion or member 894. The guide members 892 and 894 are moveable relative to each other.

The lower guide member 892 (FIG. 28) has a body 896 with a cylindrical passage 898 having a first diameter. The diameter of the passage 898 is a little larger than the diameter of the insertion rod 330. A pair of guides 900 extend upward from the body 896. The guides 900 extend transverse to the passage 898. One of the guides 900 has a slot 902 for connecting the upper guide member 894 to the lower guide member 892.

A fastener 906 extends through a washer 908 and the slot 902 in the guide 900. The fastener 906 threadably engages an opening 910 in the upper guide member 894 to interconnect the lower and upper guide members 892 and 894. The opening 910 extends into a projection 912 extending from a body 914 of the upper guide member 894.

The body 914 of the upper guide member 894 includes recesses 916, one of which is shown in FIG. 28, that receive the guides 900 of the lower guide member 892. The upper guide member 894 is received between the guides 900. The upper guide member 894 is moveable toward and away from the body 896 of the lower guide member 892.

The body 914 of the upper guide portion 894 has a cylindrical passage 918 having a second diameter smaller than the first diameter of the passage 898 in the lower guide member 892. The second diameter is a little larger than the diameter of the shaft 852 of the marker 850. The body 914 includes a slot 920 extending through an upper surface of the body. The slot 920 intersects the passage 918.

The shaft 852 of the marker 850 may be inserted through the passage 918 in the upper guide portion 894 until a radially extending positioning member 862 on the shaft 852 is received in the slot 920. The lower guide portion 892 is then telescoped over the insertion rod 330 extending from the trial sizer 300 so that the insertion rod extends into the passage 898 in the lower guide portion. As the guide portions 892 and 894 are moved axially relative to the insertion rod 330, an end portion 854 of the shaft 852 and stabilizing shafts 878 of the stabilizing member 870 are inserted into one of the vertebrae 12 and 14, such as the vertebra 12. After the marker 850 is connected to the vertebra, the guide mechanism 890 is removed from the marker and the trial sizer 300 is removed from between the vertebrae 12 and 14. The guide portions 892 and 894 move relative to each other while maintaining the passages 898 and 918 parallel to each other. The upper and lower guide members 894 and 892 may be moved relative to each other to position the marker 850 at a desired location on a desired vertebra of the spinal column. The fastener 906 may be tightened to clamp the guide 900 to the upper guide portion 894 to prevent relative movement between the lower and upper guide portions 892 and 894.

After the marker 850 is connected to the vertebra 12 and the trial sizer 300 is removed from between the vertebrae 12 and 14, the vertebrae may be cut to receive the apparatus 10. The cutters 450 and 490 may be sequentially connected to the insertion rod 330. The insertion rod 330 is placed through the passage 898 in the lower guide portion 892. The upper guide portion 894 is then telescoped over the shaft 852 of the marker 850 and the cutters 450 and 490 may sequentially cut the grooves in the vertebrae 12 and 14.

It is contemplated that the mounting members 150 or 200 may be connected to the vertebrae 12 and 14 prior to inserting the disc 26 between the vertebrae 12 and 14. The mounting members 150 or 200 may be connected to the vertebrae 12 and 14 using a surgical apparatus that includes an actuator 1002 and an insertion member 1004 (FIGS. 29-32). One of the mounting members 150 or 200 is connected to the member 1004 and the actuator 1002 moves the member to connect the mounting member to one of the vertebrae 12 and 14. The actuator 1002 (FIG. 29) may be a modular spine distractor manufactured by Friedrich GmbH of Solingen, Germany to which the member 1004 is connected. The actuator 1002 is known in the art and will not be described in detail.

The actuator 1002 includes a pair of actuation handles 1006 and a pair of separators 1008 that are connectable to the member 1004. The handles 1006 are connected to the separators 1008 by a linkage system 1010. Upon movement of the handles 1006 toward each other, the linkage system 1010 causes the separators 1008 to move away from each other. The actuator 1002 also includes a locking mechanism 1012 for locking the separators 1008 at a desired distance from each other.

The insertion member 1004 (FIGS. 30-32) is connectable to one of the separators 1008. The member 1004 includes a connecting end 1014 that is insertable into an opening (not shown) in one of the separators 1008 of the actuator 1002. The end 1014 includes a pair of projections 1016. The projections 1016 (FIG. 31) extend generally parallel to each other and define a channel 1018 between them. The end 1014 is inserted into the opening (not shown) in the separator 1008 of the actuator 1002 to connect the member 1004 to the actuator in a known manner. The member 1004 may be removed from the separator 1008 in a known manner. It is contemplated that the end 1014 of the member 1004 may have any desired configuration to connect the member to a desired actuator.

The projections 1016 (FIGS. 30-32) extend from a first end 1020 of a central body 1022 of the member 1004. The central body 1022 has an upper surface 1024 and a lower surface 1026 extending from the first end 1020 to a second end 1028 of the central body. The projections 1016 extend at an angle to the upper surface 1024 and generally parallel to the lower surface 1026. It is contemplated that the projections 1016 may extend at any desired angle to the upper surface 1024 and the lower surface 1026.

An insertion end 1030 (FIGS. 30-32) of the member 1004 extends from the second end 1028 of the body 1022. The insertion end 1030 extends at an angle to the upper surface 1024 of the body 1022 and generally parallel to the projections 1016. It is contemplated that the insertion end 1030 may extend at any desired angles relative to the upper surface 1024 and the projections 1016.

The insertion end 1030 (FIG. 31) includes a recess 1034 for receiving the mounting member 150 or 200. The recess 1034 is generally U-shaped with an open end 1036 through which the mounting member 150 or 200 may be inserted into the recess and removed from the recess. The recess 1034 is defined by a first sidewall 1038 and a second side wall (not shown) extending from the open end 1036. The first sidewall 1038 and the second sidewall are interconnected by a back wall 1042. A bottom wall 1044 extends generally perpendicular to the first sidewall 1038, the second sidewall, and the back wall 1042.

The back wall 1042 has a notch 1048 extending toward the body 1022. A groove 1050 is formed in the first sidewall 1038 and a portion of the back wall 1042. The groove 1050 extends from adjacent the open end 1036 to the notch 1048. A groove (not shown) formed in another portion of the back wall 1042 and the second sidewall (not shown) extends from the notch 1048 to adjacent the open end 1036.

A first circular opening 1056 extends through the bottom wall 1044 and is centrally located in the recess 1034. The opening 1056 permits removal of the mounting member 150 or 200 from the recess 1034 if needed. A second smaller circular opening 1058 extends through the bottom wall 1044 and is located in the notch 1048.

Figure 33:
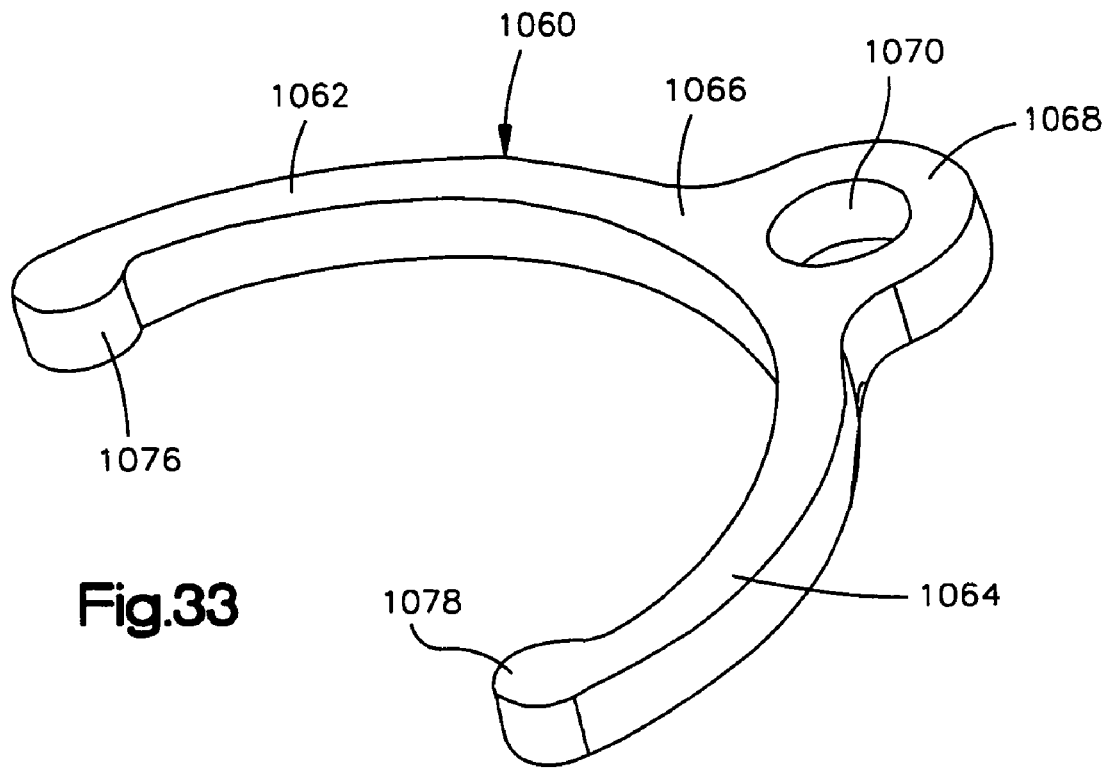
FIG. 33 is a pictorial view of a spring member for connecting a mounting member to the insertion member of FIG. 31.

A spring member 1060 (FIG. 33) is received in the recess 1034 to hold the mounting member 150 or 200 in the recess. The spring member 1060 is generally U-shaped and includes a pair of arms 1062 and 1064 extending from a base 1066. A projection 1068 extends from the base 1066 in a direction opposite from the arms 1062 and 1064. The projection 1068 has a circular opening 1070 for receiving a pin (not shown) to connect the spring member 1060 to the member 1004. The pin (not shown) extends through the opening 1070 in the spring member 1060 and into the opening 1058 in the member 1004 to connect the spring member to the member 1004.

The arm 1062 engages the mounting member 150 or 200 to retain the mounting member in the member 1004. The arm 1062 has a radially inwardly extending projection 1076. The projection 1076 extends into one of the recesses 196 or 240 in the mounting member 150 or 200 to retain the mounting member in the member 1004. The arm 1064 has a radially inwardly extending projection 1078. The projection 1078 extends into one of the recesses 196 or 240 in the mounting member 150 or 200 to retain the mounting member in the member 1004.

The spring member 1060 is inserted into the recess 1034 through the open end 1036. The arms 1062 and 1064 extend into the groove 1050 in the first sidewall 1038 and the groove (not shown) in the second sidewall (not shown) as the spring 1060 is being inserted into the recess 1034. The arms 1062 and 1064 move toward each other. When the arms 1062 and 1064 are adjacent the groove 1050 and the groove (not shown) in the second sidewall (not shown), the arms move away from each other.

When the spring 1060 is inserted in the recess 1034, the arm 1062 extends into the groove 1050 and the arm 1064 extends into the groove (not shown) in the second sidewall (not shown). The opening 1070 in the projection 1068 of the spring member 1060 is aligned with the opening 1058 in the insertion end 1030. A pin (not shown) extends through the opening 1070 in the spring member 1060 and into the opening 1058 to retain the spring member in the recess 1034.

Upon insertion of the mounting member 150 or 200 between the arms 1062 and 1064 of the spring 1060, the arms move radially outwardly away from each other until the recesses 196 or 240 are aligned with the projections 1076 and 1078. When the recesses 196 or 240 are aligned with the projections 1076 and 1078, the arms 1062 and 1064 move toward each other into the recesses to retain the mounting member 150 or 200 in the insertion end 1030. The mounting member 150 or 200 may be removed from the recess 1034 by overcoming the retaining force applied by the spring member 1060.

The insertion end 1030 of the member 1004 includes recesses 1082. The recesses 1082 are located on opposite sides of the open end 1036 of the recess 1034. The recesses 1082 are used to ensure insertion of the mounting member 150 or 200 to a desired depth in one of the vertebrae 12 and 14.

A guide member 1100 (FIGS. 30 and 34) may be used to guide insertion of the mounting members 150 or 200 into the vertebrae 12 and 14. The guide member 1100 has a shape similar to the apparatus 10 and may be wedge shaped. The guide member 1100 has a first, distal or posterior end 1102 and an opposite, second proximal or anterior end 1104. The guide member 1100 also includes first and second lateral sides 1106 and 1108 extending between the first end second ends 1102 and 1104. An upper surface 1110 of the guide member 1100 is engageable with the vertebra 12 and a lower surface 1112 is engageable with the vertebra 14. Each of the upper and lower surfaces 1110 and 1112 have a plurality of rails 1114 for slidably engaging grooves cut in the vertebrae 12 and 14 by the cutters 450 and/or 490. The ribs 1114 extend from the second end 1104 toward the first end 1102. It is contemplated that the rails 1114 may cut grooves in the vertebrae 12 and 14.

Figure 30:
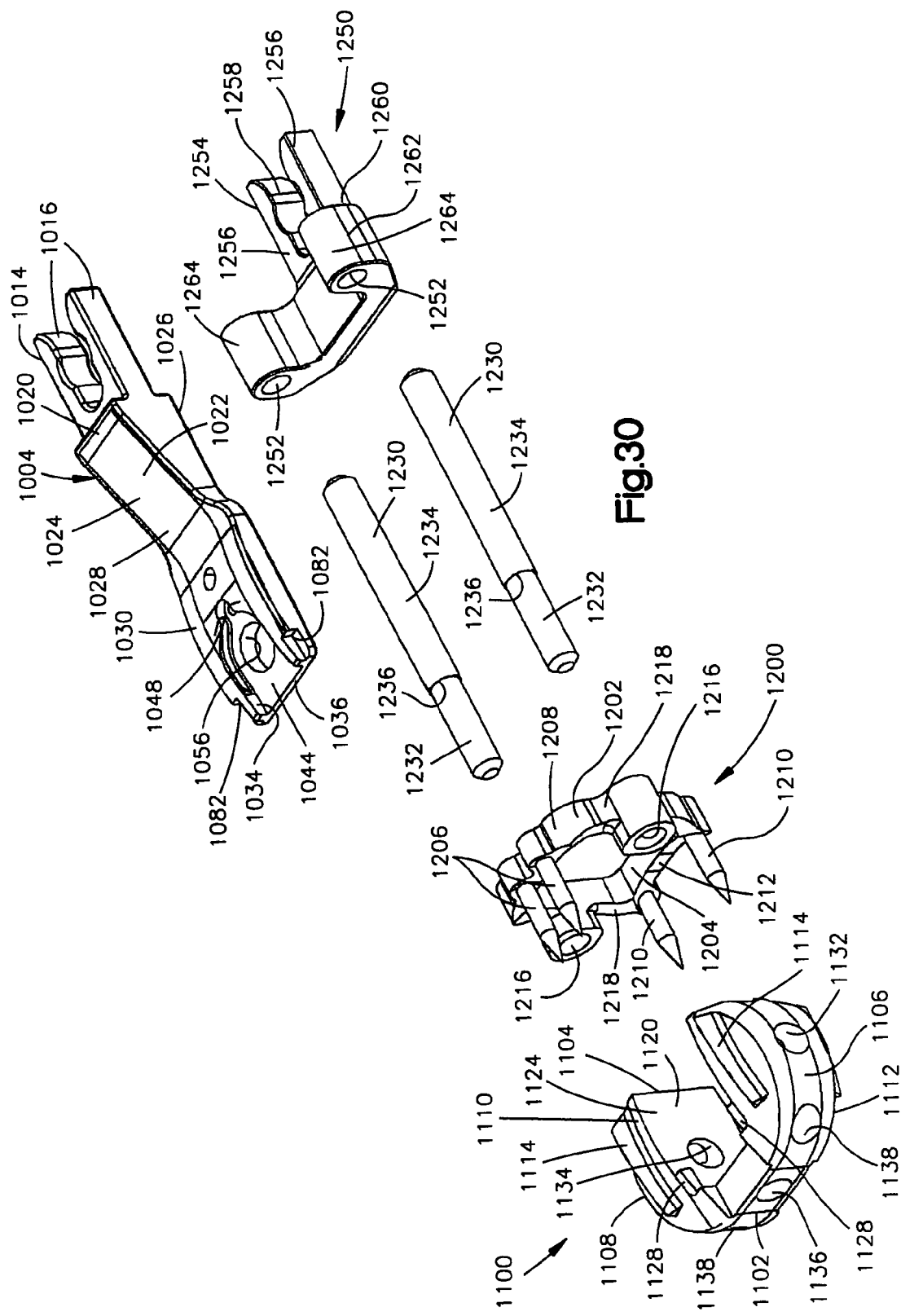
FIG. 30 is an exploded pictorial view of an insertion assembly for use with the actuator of FIG. 29.
Figure 31:
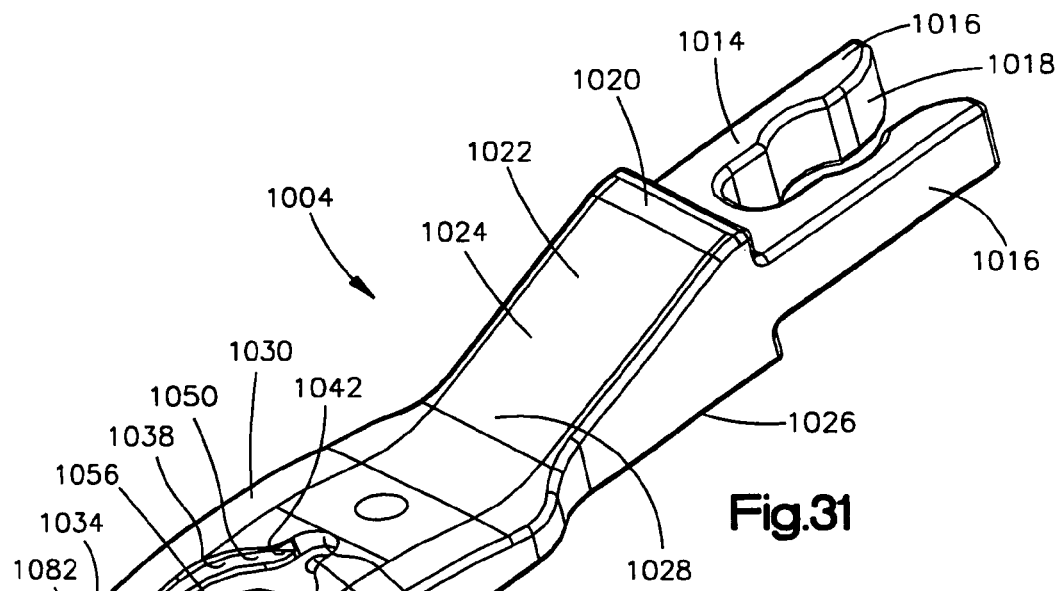
FIG. 31 is an enlarged pictorial view of an insertion member of the assembly of FIG. 30.
Figure 32:
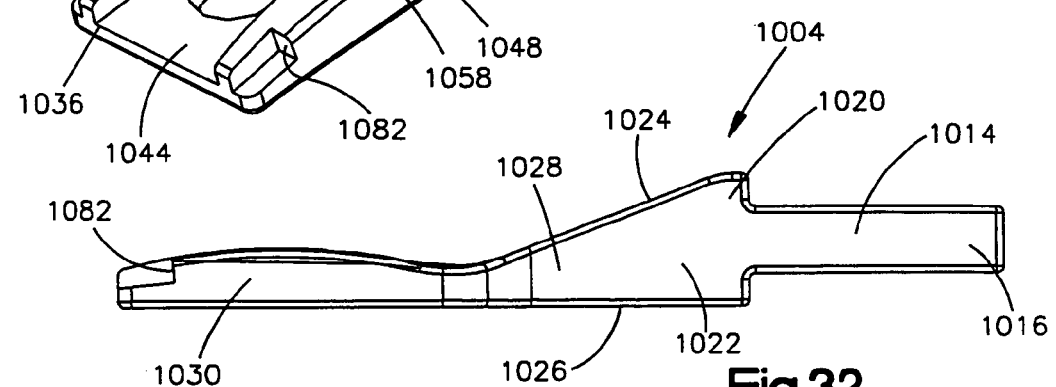
FIG. 32 is a schematic side view of the insertion member of FIG. 31.
Figure 34:
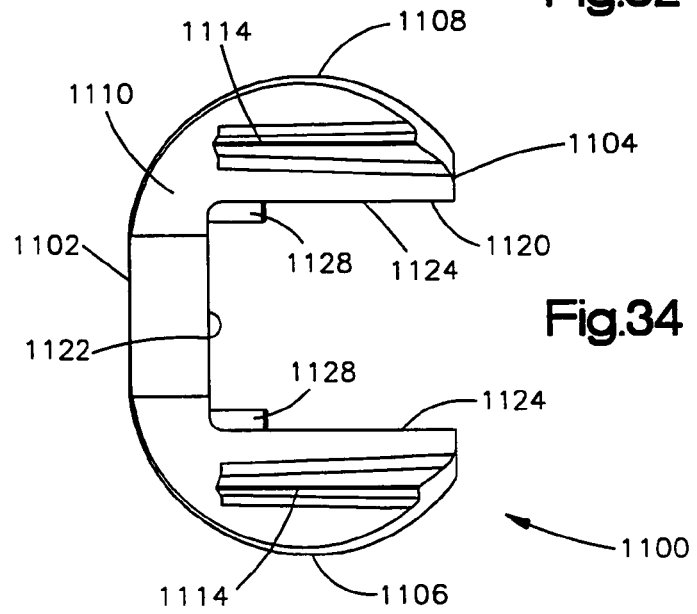
FIG. 34 is a schematic top view of a guide member of the assembly of FIG. 30.

The guide member 1100 (FIG. 34) includes a recess 1120 extending from the second end 1104 toward the first end 1102. An end wall 1122 and sidewalls 1124 of the guide member 1100 define the recess 1120. The end wall 1122 and the sidewalls 1124 are engageable with the insertion member 1004 to guide movement of the insertion member relative to the vertebrae 12 and 14. Four flanges 1128, two of which are shown in FIGS. 30 and 34, extend from the end wall 1122 and the side walls 1124 into the recess 1120. The flanges 1128 extend into the recesses 1082 on the insertion member 1004 and engage the insertion member 1004 to prevent further insertion of the mounting member 150 or 200 into one of the vertebrae 12 and 14.

The guide member 1100 (FIG. 30) includes a passage 1132 extending from the first lateral side 1106 into the recess 1120. A passage 1134 extends from the second lateral side 1108 into the recess 1120. The passages 1132 and 1134 are coaxial. The guide member 1100 includes a central cylindrical passage 1136 extending from the posterior side 1102 into the recess 1120. The guide member 1100 also includes two lateral cylindrical passages 1138 extending between the first and second ends 1102 and 1104. The passages 1136 and 1138 extend generally parallel to each other. The passages 1138 intersect the passages 1132 and 1134. It is contemplated that the passages 1132, 1134, 1136, and 1138 may have any desired configuration. The passages 1132, 1134, 1136, and 1138 may be viewed using an imaging system, such as fluoroscopy, to determine if the guide member 1100 is properly positioned between the vertebrae 12 and 14. When the guide member 1100 is properly positioned between the vertebrae 12 and 14, the passages 1132, 1134, 1136, and 1138 may appear as circles in an image produced by the imaging system. The passages 1132, 1134, 1136, and 1138 may appear as ovals in an image when the guide member 1100 is not properly positioned. The passage 1136 may be threaded to receive the insertion rod 330.

The insertion rod 330 may threadably engage the passage 1136. The insertion rod 330 may be used for inserting the guide member 1100 between the vertebrae 12 and 14. The insertion rod 330 may be inserted into the passage 398 of the guide assembly 351 or the passage 898 of the guide assembly 851. The guide mechanism 390 or guide mechanism 890 is then telescoped over the shaft 352 or 852 of the marker 350 or 850 until the recess 408 or slot 920 receives the radially extending positioning members 362 or 862 on the shaft 352 or 852. Accordingly, the guide member 1100 is in a desired alignment with the vertebrae 12 and 14. The insertion rod 330 may be struck with a mallet or hammer to cause the guide member 1100 to move between the vertebrae 12 and 14.

Figure 35:
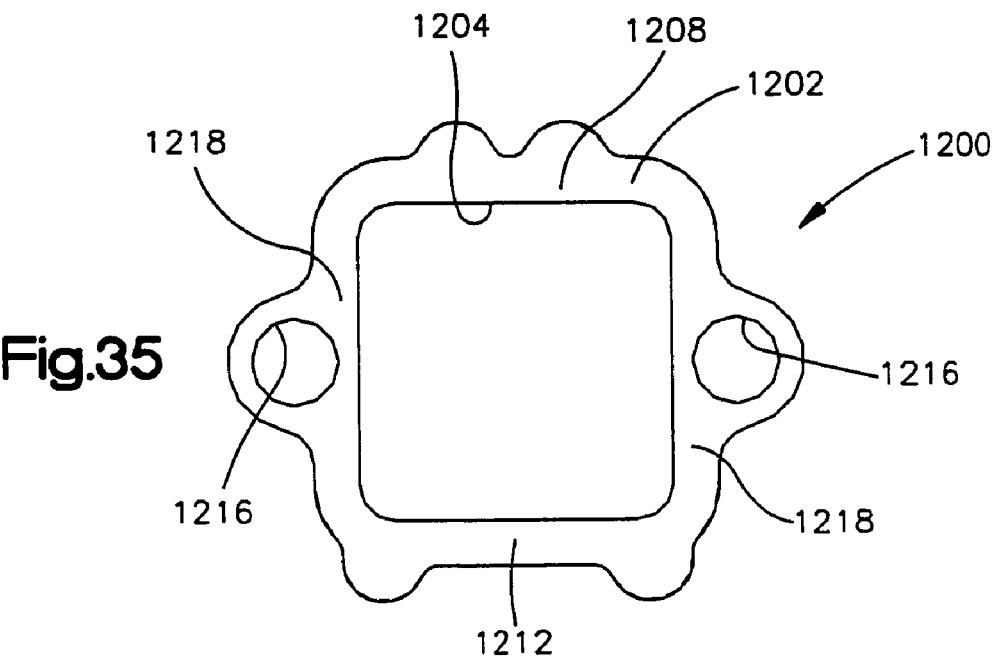
FIG. 35 is a schematic plan view of a vertebral stabilizer of the assembly of FIG. 30.

A vertebral stabilizer 1200 (FIGS. 30 and 35) is engageable with the vertebrae 12 and 14 to prevent relative movement between the vertebrae during insertion of the mounting members 150 or 200. The vertebral stabilizer 1200 includes a generally square shaped body 1202 defining a central passage 1204. Upper mounting shafts 1206 extend from a central portion of an upper wall 1208 of the body 1202. The upper mounting shafts 1206 are engageable with the vertebra 12 to connect the vertebral stabilizer 1200 with the vertebra 12. Lower mounting shafts 1210 extend from laterally outer portions of a lower wall 1212 of the body 1202. The lower mounting shafts 1210 are engageable with the vertebra 14 to connect the vertebral stabilizer 1200 with the lower vertebra 14. Accordingly, the vertebral stabilizer 1200 prevents relative movement between the vertebrae 12 and 14 when the stabilizer is connected with the vertebrae.

The vertebral stabilizer 1200 includes openings 1216 in side walls 1218 of the body 1202. The openings 1216 are aligned with the passages 1138 in the guide member 1100 when the vertebral stabilizer is connected to the vertebrae 12 and 14. The openings 1216 in the vertebral stabilizer 1200 and the passages 1138 in the guide member 1100 receive positioning rods 1230 (FIG. 30). Each of the rods 1230 includes a first axial end portion 1232 with a first diameter. Each of the rods 1230 includes a second axial end portion 1234 with a second diameter larger than the first diameter. A radially extending surface 1236 extends between the first and second axial end portions 1232 and 1234. The first axial end portions 1232 are inserted into the openings 1216 in the vertebral stabilizer 1200 and the passages 1138 of the guide member 1100 until the radially extending surfaces 1236 engage the vertebral stabilizer.

A member 1250 (FIG. 30) has openings 1252 for receiving the second end portions 1234 of the rods 1230. The member 1250 is connectable to one of the separators 1008 of the actuator 1002. The member 1250 includes a connecting end 1254 that is insertable into an opening (not shown) in one of the separators 1008 of the actuator 1002. The end 1254 includes a pair of projections 1256. The projections 1256 extend generally parallel to each other and define a channel 1258 between them. The end 1254 is inserted into the opening (not shown) in the separator 1008 of the actuator 1002 to connect the member 1250 to the actuator in a known manner. The member 1250 may be removed from the separator 1008 in a known manner. It is contemplated that the end 1254 of the member 1250 may have any desired configuration to connect the member to a desired actuator.

The projections 1256 extend from a first side 1260 of a body 1262 of the member 1250. The body 1262 is generally U-shaped with upper ends 1264. The openings 1252 extend through the upper ends 1264 of the body 1262.

When one of the mounting members 150 or 200 is to be connected to one of the vertebrae 12 and 14, the guide member 1100 is inserted between the vertebrae. The rods 1230 are placed through the openings 1216 in the vertebral stabilizer 1200. The vertebral stabilizer 1200 is connected to the vertebrae 12 and 14 with the rods 1230 extending into the passages 1138 in the guide member 1100. The insertion member 1004 and the member 1250 are connected to the separators 1008 of the actuator 1002. The mounting member 150 or 200 is connected with the insertion member 1004. The insertion member 1004 is placed through the opening 1204 in the vertebral stabilizer 1200 and into the recess 1120 in the guide member 1100. The insertion member 1004 is inserted into the recess 1120 in the guide member so that the insertion member engages the end wall 1122 defining the recess 1120. As the insertion member 1004 is inserted through the opening 1212 in the vertebral stabilizer 1200, the member 1250 is placed over the rods 1230 so that the rods extend through the openings 1252 in the member 1250. Accordingly, the member 1250 cannot move relative to the vertebrae 12 and 14.

The insertion member 1004 is moved away from the member 1250 by the actuator 1002 to connect the mounting member 150 or 200 to the vertebra 12. The vertebral stabilizer 1200 prevents relative movement between the vertebrae 12 and 14. After the mounting member 150 or 200 is connected to the vertebra 12, the actuator 1002 may be turned over and the other mounting member 150 or 200 may be connected to the vertebra 14.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, we claim:

1. An apparatus for replacing a spinal disc in a spinal column, said apparatus comprising:
    a first end;
    a second opposite end;
    first and second lateral sides extending between said first and second ends;
    an outer surface engageable with a first vertebra of the spinal column;
    first and second rails extending from said outer surface, said first rail having a length extending generally transverse to said first and second ends, said second rail having a length extending generally transverse to said first rail, said first rail including a plurality of projections extending from said outer surface;
    a resilient core having a first surface and a second surface;
    a first retaining device connected to said first surface of said resilient core, said first retaining device having said outer surface engageable with the first vertebra of the spinal column and an inner surface facing said first surface of said resilient core, said first retaining device including a first mounting member and a first retaining member, said first retaining member having an inner surface affixed to said first surface of said core, said first mounting member including an inner surface facing said core and spaced from said first surface of said core, said first mounting member including said first and second rails; and
    a second retaining device connected to said second surface of said resilient core, said second retaining device having an outer surface engageable with a second vertebra of the spinal column and an inner surface facing said second surface of said resilient core.

2. An apparatus as set forth in claim 1 wherein said first and second rails have lengths extending generally perpendicular to each other.

3. An apparatus as set forth in claim 1 wherein said first rail includes a recess for providing bony ingrowth.

4. An apparatus as defined in claim 1 wherein said first retaining member has an opening extending through said inner and outer surfaces of said first retaining member, said first mounting member being located in said opening.

5. An apparatus as defined in claim 4 wherein said opening extends axially through said first retaining member.

6. An apparatus as defined in claim 4 wherein said first mounting member is connected to said first retaining member.

7. An apparatus as defined in claim 6 wherein said first mounting member is prevented from moving relative to said first retaining member.

* * * * *